US012807984B2

(12) United States Patent
Lanfear

(10) Patent No.: US 12,807,984 B2
(45) Date of Patent: Nov. 24, 2026

(54) POLYGENIC SCORE FOR CARDIAC HEART FAILURE

(71) Applicant: Henry Ford Health System, Detroit, MI (US)

(72) Inventor: David Ethan Lanfear, Birmingham, MI (US)

(73) Assignee: Henry Ford Health System, Detroit, MI (US)

( * ) Notice: Subject to any disclaimer, the term of this patent is extended or adjusted under 35 U.S.C. 154(b) by 1086 days.

(21) Appl. No.: 17/642,577

(22) PCT Filed: Sep. 13, 2020

(86) PCT No.: PCT/US2020/050602
§ 371 (c)(1),
(2) Date: Mar. 11, 2022

(87) PCT Pub. No.: WO2021/051033
PCT Pub. Date: Mar. 18, 2021

(65) Prior Publication Data

US 2022/0333169 A1 Oct. 20, 2022

Related U.S. Application Data

(60) Provisional application No. 62/900,219, filed on Sep. 13, 2019.

(51) Int. Cl.

| | |
|---|---|
| ***C12Q 1/6827*** | (2018.01) |
| ***A61K 31/138*** | (2006.01) |
| ***A61K 31/165*** | (2006.01) |
| ***A61K 31/166*** | (2006.01) |
| ***A61K 31/404*** | (2006.01) |
| ***A61P 9/04*** | (2006.01) |
| ***C12Q 1/6858*** | (2018.01) |

(52) U.S. Cl.
CPC .......... *C12Q 1/6827* (2013.01); *A61K 31/138* (2013.01); *A61K 31/165* (2013.01); *A61K 31/166* (2013.01); *A61K 31/404* (2013.01); *A61P 9/04* (2018.01); *C12Q 1/6858* (2013.01); *C12Q 2600/106* (2013.01); *C12Q 2600/156* (2013.01)

(58) Field of Classification Search
CPC ............................ C12Q 1/6827; C12Q 1/6858
See application file for complete search history.

(56) References Cited

U.S. PATENT DOCUMENTS

| | | | | |
|---|---|---|---|---|
| 2005/0019776 A1 | | 1/2005 | Callow et al. | |
| 2008/0274471 A1* | | 11/2008 | Cohen .................. | C12Q 1/6883 435/6.11 |
| 2014/0303013 A1* | | 10/2014 | Hageman ............. | A61K 31/225 506/9 |
| 2019/0017120 A1 | | 1/2019 | Soykan et al. | |
| 2020/0027557 A1* | | 1/2020 | Karow ................... | G16H 50/50 |

FOREIGN PATENT DOCUMENTS

| | | | | |
|---|---|---|---|---|
| CA | 2844103 C * | 3/2019 | ................ | A61P 9/00 |
| WO | WO-2016167408 A1 * | 10/2016 | ............. | G16B 30/00 |

OTHER PUBLICATIONS

Cresci et al., Interaction between PPARA genotype and beta-blocker treatment influences clinical outcomes following acute coronary syndromes 2008 Pharmacogenetics 10: 1403-1417. (Year: 2008).*
Roden et al., The genetic basis of variablity in drug response. 2002 Nature Reviews, 1: 37-44 (Year: 2002).*
Muthumala et al, Role of beta andrenergic receptor polymorphisms in heart failure: systematic review and meta-analysis. 2008, 10:3-13 (Year: 2008).*
Parikh, K et al,Dose Response of B-Blockers in Adrenergic Receptor Polymorphism Genotypes, 2018, Circ Genom Precis Med. Aug. 2018;11:e002210 (Year: 2018).*
Pocock, S. et al., Predicting survival in heart failure: a risk score based on 39372 patients from 30 studies, Euro Heart Jour (2013) 34,1404-1413 (Year: 2013).*
WO 2016167408 english translation of document. (Year: 2016).*
Rich, J., et al., Meta-analysis global group in chronic (MAGGIC) heart failure risk score: validation of a simple tool for the prediction of morbidity and mortality in heart failure with preserved ejection fraction, J Am Heart Assoc Oct. 2018; 7:e009594 (Year: 2018).*
Heidecker B., et al. Transcriptomic analysis identifies the effect of beta-blocking agents on a molecular pathway of contraction in the heart and predicts response to therapy, 2016, Jour Am Coll Cardiol Basic Trans Sci, 1: 107-121 (Year: 2016).*
Cresci, S. et al. "Interaction between PPARA genotype and (Beta-blocker treatment influences clinical outcomes following acute coronary syndromes," Pharmacogenomics, Oct. 14, 2008, vol. 9, No. 10, pp. 1403-1417.
Evans, K. et al. "Genetics of heart rate in heart failure patients (GenHRate)," Human Genomics, May 21, 2019, vol. 13, No. 22, pp. 1-11.
Goldberger, J. et al. "Effect of Beta-Blocker Dose on Survival after Acute Myocardial Infarction," Journal of American College of Cardiology, Sep. 29, 2015, vol. 66, Iss. 13, pp. 1431-1441.
International Search Report for PCT/US2020/050602, mailed Dec. 21, 2020, 3 pgs.
Parikh, K. et al. "Dose Response of Beta-Blockers in Adrenergic Receptor Polymorphism Genotypes," Circulation: Genomic and Precision Medicine, Aug. 13, 2018, vol. 11, No. 8, pp. 1-14.

* cited by examiner

*Primary Examiner* — Neil P Hammell
*Assistant Examiner* — Lisa Horth
(74) *Attorney, Agent, or Firm* — Reising Ethington P.C.

(57) ABSTRACT

The present disclosure provides methods for creation, validation and application of a polygenic response predictor (PRP) score which can identify and/or predict beta-blocker survival benefit in heart failure. In one aspect, provided herein are systems and methods for identifying, diagnosing, and treating heart failure patients of European descent who are likely to respond to beta-blocker treatment.

17 Claims, 7 Drawing Sheets

POLYGENIC SCORE FOR CARDIAC HEART FAILURE

CROSS REFERENCE TO RELATED APPLICATIONS

This application is a 35 U.S.C. § 371 National Stage filing of International Application No. PCT/US2020/050602, filed Sep. 13, 2020, which claims the benefit of, and priority to, U.S. Provisional Application No. 62/900,219, filed on Sep. 13, 2019. The entire contents of the aforementioned applications are incorporated herein by reference in their entireties.

GOVERNMENT LICENSE RIGHTS

This invention was made with government support under R01 HL103871 and R01HL132154 awarded by National Institute of Health (NIH). The government has certain rights in the invention.

FIELD OF THE INVENTION

The present disclosure relates to methods for creation, validation and application of a polygenic score which can identify and/or predict beta-blocker survival benefit in subjects with heart failure.

BACKGROUND

Beta-blockers (BB) are one of the most important therapeutic options for heart failure (HF), especially those with reduced ejection fraction (HFrEF). However, individual responses to BB treatment vary. Improved methods to identify patients that are good candidates for BB treatment are needed. The present disclosure provides methods for identification of patients that are BB responders versus non-responders, and to derive and validate the first polygenic response predictor (PRP) for BB survival benefit in heart failure (HF) patients.

Beta-blockers (BB) are one of the most important treatments for heart failure. Despite BB importance in the clinic, individual responses to BB treatment vary. The observed variation in response to BB may be due, in part, to genetic variation. However, individual SNPs have not proven clinically useful to target treatment. The present disclosure provides an unbiased robust approach to identify a multi-genetic marker profile of BB effectiveness. The presently disclosed approach provides insights about treatment-specific survival prediction by combining multiple genetic markers identified using a genome-wide (GW) approach.

The landmark beta-blocker (BB) clinical trials for heart failure with reduced ejection fraction (HFrEF) showed a significant reduction in the risk of death overall, (1-3) but it is important to point out that individual patient responses to BB widely vary. For example, in one randomized clinical trial, the 95% confidence interval for change in left ventricular ejection fraction (LVEF) with carvedilol was −11.1 to +32.9. (4) Despite this well-recognized variability BB response, (5) current guidelines for HF correctly adopt a "one size fits all" approach, whereby all patients are recommended to be treated with the same target doses of BB,6 because clinical characteristics largely did not impact HF patients' response to BB therapy in terms of survival. (1-3) A relatively recent possible exception to this is atrial fibrillation, which some studies have reported negates BB effectiveness in HF. (7, 8) Since clinical factors are largely unable to identify BB responders vs. non-responders, understandably much research has focused on other factors, such as genetic variation, to support precision medicine approaches for BB treatment decisions. (9-11) These pharmacogenetic studies, mostly employing the candidate gene approach, (12-16) generally support the concept that genetic variation impacts BB response in HF patients but results are inconsistent and no clinically actionable markers are proven to date. (17) Although there are some examples where one or two genetic variants (usually in the setting of altered drug metabolism) have sufficient impact on drug response to generate a clinical action (e.g. CYP2C19 and clopidogrel) (18), it now appears that common complex phenotypes are likely under the influence of many genetic loci, each variant acting with relatively small impact, (19-21) and drug response may be similarly complex and polygenic in nature.

Polygenic risk scores have emerged as a method to aggregate the small effects of numerous genetic variants into a score that reflects the overall genetic risk of a phenotype of interest. For common complex traits, this appears to often capture enough variation for clinical utility, where a smaller number of genome-wide significant "hits" have failed to do so. (22, 23) Polygenic scores have now been developed for several common diseases, such as coronary disease and others, (23, 24) and these will soon be explored for implementation of targeted population management. Despite this exciting new development, similar analytic methods have largely not yet been successfully adapted to drug response in the setting of prevalent disease.

There are emerging examples published, (10, 25-34) but to our knowledge, none applied to treatment of HF. Limited adaptation of polygenic scores to drug-response may be due in part to methodologic challenges, such as lack of sufficiently detailed drug exposure data and complexities of analysis. Although cohorts with detailed drug exposure information tend to be smaller in size relative to recent genome-wide association study (GWAS), a polygenic score approach may offer enhanced power and an efficient approach for constructing polygenic drug-response scores could have broad impact on precision medicine and drug development. The present disclosure advances over the existing art, by illustrating a way to derive and validate the first polygenic response predictor (PRP) for BB-associated survival benefit in patients with HF.

SUMMARY

In one aspect, provided herein are systems and methods for identifying, diagnosing, and treating heart failure patients of European descent who are likely to respond to beta-blocker treatment. The present invention is based, at least in part on the recognition that many common genetic variants each with modest effect sizes can contribute to a person's response to beta-blocker treatment within the disease of heart failure, and in aggregate, a polygenic response predictor score can explain and predict the likelihood that a heart failure subject will derive a survival benefit due to beta-blocker administration.

In one aspect, the invention concerns a method for assessing a human subject's likelihood to respond to beta-blocker treatment during the subject's course of heart failure treatment comprising determining in a biological sample from the subject the presence or absence of risk alleles of common allelic variants associated with beta-blocker efficacy at a plurality of independent loci.

In some embodiments, the method comprises calculating a polygenic response predictor score (PRP) for beta-blocker survival benefit in heart failure subjects. In some embodiments, the PRP defined using a random subset of heart failure patients of European descent. The PRP is constructed from a genome-wide analysis of beta-blocker genotype interaction predicting time to all-cause mortality, adjusted for a MAGGIC score, genotype, level of beta-blocker exposure, and a beta-blocker propensity score as shown in FIGS. 4A, 4B and 4C.

In some embodiments, identifying the presence of relevant SNPs that are used in the determination of the subject's PRP comprises measuring the presence of the at least 42 SNPs in the biological sample, of which at least twenty (20) SNPs are used to calculate the PRP. In some embodiments, the method further comprises assigning the subject to a risk group having a specified PRP cutoff score which separates responders from non-responders based on the PRP. In some embodiments, method further comprises an initial step of obtaining a biological sample from the subject. In some embodiments, at least 10,000 SNPs are identified. In some embodiments, at least 5,000 SNPs, or at least 4,500 SNPs, or at least 4,000 SNPs, or at least 3,500 SNPs, or at least 3000 SNPs, or at least 2500 SNPs, or at least 2000 SNPs are identified of which at least 44, or 43, or 42 or 41 of the highest relevant SNPs are counted in accordance with Table 1 in the calculation of the PRP in accordance with the method described in FIGS. 4A, 4B and 4C.

In some embodiments, the identified SNPs comprise the beta-blocker drug effect SNPs. In some embodiments, the identified SNPs comprise rs4331189, rs4075503, rs16870234, rs75087282, rs28548659, rs782760, rs367841, rs6013374, rsl89508091, rs299453, rs299445, rs9737956, rs6773175, rs34912, rs2457492, rs2225686, rs299468, rs34221557, and rs60529740, and rsl0810237.

In some embodiments, the method further comprises initiating a beta-blocker treatment to the subject having been determined as a likely responder based on the calculated PRP score. In some embodiments, the treatment is determined or adjusted according to the PRP score and determination whether the subject is a likely responder or non-responder. In some embodiments, identifying whether the SNP is present comprises sequencing at least part of a genome of one or more cells from the subject. In some embodiments, the subject is a white or Caucasian human of European descent. In some embodiments, the heart failure is systolic heart failure. In some embodiments, the heart failure is New York Heart Association (NYHA) Functional Classification class I, II, III, or IV, each with an objective assessment ranging from A-D. In some embodiments, sequencing comprises whole genome sequencing.

In another aspect, the invention relates to a method of determining a beta-blocker polygenic response predictor score (PRP) for beta-blocker survival benefit in a heart failure subject of European descent, the method comprising selecting at least 20 single nucleotide polymorphisms (SNPs) from Table I; identifying whether the at least 20 SN-Ps are present in a biological sample from the subject; and calculating the polygenic response predictor score (PRP) based on the presence of the SNPs.

In another embodiment, the subject has been diagnosed with early stage heart failure.

In yet another embodiment, the subject has been diagnosed with intermediate heart failure.

In a still further embodiment, determining the presence of absence of one or more risk alleles is achieved by amplification of nucleic acid from said sample.

In various embodiments, amplification may comprise PCR, amplification may be located on a chip, where primers for amplification are specific for alleles of the common genetic variants tested.

In a particular embodiment, the amplification comprises: (i) admixing an amplification primer or amplification primer pair with a nucleic acid template isolated from the biological sample, wherein the primer or primer pair is complementary or partially complementary to a region proximal to or including the polymorphism, and is capable of initiating nucleic acid polymerization by a polymerase on the nucleic acid template; and, b) extending the primer or primer pair in a DNA polymerization reaction comprising a polymerase and the template nucleic acid to generate the amplicon.

The amplicon may, for example, be detected by a process that includes one or more of hybridizing the amplicon to an array, digesting the amplicon with a restriction enzyme, or real-time PCR analysis.

In another embodiment, the amplification comprises performing a polymerase chain reaction (PCR), reverse transcriptase PCR (RT-PCR), or ligase chain reaction (LCR) using nucleic acid isolated from the organism or biological sample as a template in the PCR, RT-PCR, or LCR.

In yet another embodiment, the method may further comprises cleaving amplified nucleic acid.

A further embodiment, the biological sample is derived from a bodily fluid, such as saliva or blood.

In other embodiments, the method further comprises the step of making a decision on the timing and/or frequency of beta-blocker responsiveness diagnostic testing for the subject and/or on the timing and/or frequency of beta-blocker treatment for the subject of European ancestry/descent who is diagnosed with heart failure.

In a still further embodiment, the method comprises determination of the presence or absence of risk alleles for all single nucleotide polymorphisms set forth in Table 1, and the beta-blocker polygenic response predictor (PRP) score is calculated based on such determination, and provided in FIGS. 4A, 4B and 4C.

In another embodiment, the method further comprises the step of recording the results of said determination on a computer readable medium.

In yet another embodiment, the results are communicated to the subject or the subject's physician and/or are recorded in the form of a report.

In another aspect, the invention concerns a report comprising the results of the methods herein.

The device integrates multimodal data, is quantitative rather than qualitative, is objective rather than subjective, and also provides an option for outputting actionability (e.g., steps that can be taken to counter the increased risk). The systems and methods can be implemented in a minimally invasive manner, wherein the only invasive component is a routine blood draw. Actionability permits identification of factors that an individual may modify to improve their prognosis. Moreover, early screening may reduce or even eliminate psychological tension and even with a positive diagnosis, an at-risk patient can take steps to mitigate the risk.

In some embodiments, the disclosure relates to a computer readable medium comprising computer-executable instructions, which, when executed by a processor, cause the processor to carry out a method or a set of steps for diagnosing beta-blocker responsiveness which results in a statistically significant outcome in the treatment of heart failure in a heart failure subject of European ancestry or descent, the method or steps comprising, a) extracting, into a diagnostic model, a plurality of features comprising (1) at least 20 SNPs from the group of 44 SNP's in Table 3; b) mathematically calculating a polygenic response predictor score which is calculated using Formula (I):

$$\text{score} = \sum_{j=1}^{x} w_j * SNP_j, \tag{Formula (I)}$$

wherein the score is the sum of the SNP weight ($w_j$) multiplied by the SNP genotype ($SNP_j$) (0, 1, 2) summed over all the SNPS in the score (any number of SNPs ranging from 20 to 44 of the SNPs listed in Table 3); and outputting a beta-blocker polygenic response predictor (PRP) score based on the summed scores; and d) diagnosing whether the heart failure patient is a responder or non-responder to beta-blocker treatment based on the beta-blocker polygenic response predictor score, wherein the beta-blocker responder has a PRP score of 12 or less when 20 SNPs are used or a PRP score of 68 or less when 41 to 44 SNPs from Table 3 are used.

In some embodiments, the disclosure relates to a computer readable media of the foregoing or following, wherein the processor to carries out a method or a set of steps for diagnosing whether a white subject of European ancestry/descent having heart failure (NYHA I-IV) will be a responder or a non-responder to beta-blocker treatment, i.e. whether the beta-blocker administration will provide a survival benefit, the method or steps comprising, a) extracting, into the diagnostic model, a plurality of genetic features related to SNPs that are provided in Table 1; b) computing the PRP score as a function of $$\text{score} = \sum_{j=1}^{x} w_j * SNP_j, \tag{Formula I}$$

and c) comparing the PRP score for the subject and determining whether the subject's PRP score is above or below the responder PRP score threshold of less than about 68 when 41 to 44 SNPs from Table 3 are imputed into the calculation of the PRP score, wherein if the subject's PRP score is below the responder's PRP score of about 68 or less when 41 to 44 SNPs from Table 3 are used, then the subject is scored as a responder to beta-blocker treatment and is administered a beta-blocker for the treatment of heart failure.

In some embodiments, the disclosure relates to a computer readable media of the foregoing or following, wherein the genetic features comprises at least 20, 21, 22, 23, 24, 25, 26, 27, 28, 29, 30, 31, 32, 33, 34, 35, 36, 37, 38, 39, 40, 41, 42, 43, or all of the genetic SNPs of Table 3, wherein the genetic features are listed in decreasing order of relevance to the beta-blocker polygenic response predictor (PRP) score. In various embodiments, the relevance is the relative weight assigned to the genetic feature when calculating the PRP score.

In some embodiments, the disclosure relates to a computer readable media of the foregoing or following, wherein the genetic features comprises at least 20, 21, 22, 23, 24, 25, 26, 27, 28, 29, 30, 31, 32, 33, 34, 35, 36, 37, 38, 39, 40, 41, 42, 43, or all of the genetic SNPs of Table 3, wherein the genetic features are listed in decreasing order of relevance to the beta-blocker polygenic response predictor (PRP) score, or a locus related thereto.

In some embodiments, the disclosure relates to a computer readable media of the foregoing or following, wherein the genetic features comprises at least 20, 21, 22, 23, 24, 25, 26, 27, 28, 29, 30, 31, 32, 33, 34, 35, 36, 37, 38, 39, 40, 41, 42, or all of the genetic SNPs of Table 3, wherein the genetic features are listed in decreasing order of relevance to the beta-blocker polygenic response predictor (PRP) score. having the Ref SNP ID Nos. rs429358; rsl1218343; rs6733839; rs6656401; rs9331896; rs4147929; rsl0792832; rsl7125944; rs7274581; rs983392; rsl1771145; rs9271192; rsl0948363; rs28834970; rsl0498633; rsl476679; rsl0838725; rs35349669; rsl90982; rs2718058 or a locus related thereto.

In some embodiments, the disclosure relates to a computer readable media of the foregoing or following, wherein the genetic features comprise genetic variations comprising SNPs and/or CNVs the method includes calculation of a beta-blocker polygenic response predictor score for subjects who are white of European ancestry which have been diagnosed as having heart failure.

In some embodiments, the disclosure relates to a computer readable media of the foregoing or following, wherein the beta-blocker polygenic response predictor score is calculated by summation of the number of risk alleles carried by an individual for each variant, weighted by the effect size from a genome-wide association study, according to Formula (I):

$$\text{score} = \sum_{j=1}^{x} w_j * SNP_j. \tag{Formula I}$$

In some embodiments, the present disclosure provides a method of treating a white subject of European ancestry suffering from heart failure, comprising: a) obtaining a nucleic acid sample from the subject; b) detecting in the nucleic acid sample of the subject the presence or absence of a plurality of single nucleotide polymorphisms (SNPs) required for the determination of a beta-blocker polygenic response predictor (BB-PRP) score indicative of the likelihood of survival benefit of beta-blocker treatment; c) identifying the subject as: i) BB responder; or ii) BB non-responder; and d) administering treatment to the subject identified in step c(i), wherein the treatment comprises a beta-blocker drug.

In some embodiments, the present disclosure provides a method of treating a subject suffering from heart failure, comprising: a) sequencing or genotyping a nucleic acid sample from the subject; b) detecting in the nucleic acid sample of the subject the presence or absence of a plurality of single nucleotide polymorphisms (SNPs) required for the determination of a beta-blocker polygenic response predictor (BB-PRP) indicative of the likelihood of survival benefit of beta-blocker treatment; c) identifying the subject as a: i) BB responder; or ii) BB non-responder; and d) administering treatment to the subject identified in step c(i), wherein the treatment comprises a beta-blocker drug.

In some embodiments, the present disclosure provides a method of treating a subject suffering from heart failure, comprising: a) detecting in cells of the subject the presence or absence of a variance in each single nucleotide polymorphism (SNP) of Table 2, wherein the combination of the presence or absence of the variance for each SNP is indicative that said treatment will be effective, more effective, less effective or ineffective in the subject; and b) administering to the subject a treatment comprising a beta-blocker drug based on detection in step (a) indicative of an effective or more effective treatment for the subject.

In another aspect, the invention relates to a method of determining whether a heart failure subject will benefit from beta-blocker therapy, the method comprising obtaining a biological sample from the subject; identifying whether at least twenty from a pool of at least 44 specific single nucleotide polymorphisms (SNPs) from Table 3 is present in the biological sample from the subject and, optionally, calculating a polygenic response predictor (PRP) score in accordance to Formula (I); wherein a PRP score of 12 or less when the top 20 SNPs from Table 3 are used in Formula (I), or a PRP score of 68 when the top 41 to 44 of the SNPs in Table 3 are used to calculate the PRP score in accordance to Formula (I) indicates that the subject is a responder to beta-blocker treatment in a heart failure setting. If the subject has a PRP score of greater than 12 when the top 20 SNPs from Table 3 are used, or a PRP score of greater than 68 when the Top 41-44 SNPs from Table 3 are used in Formula (I), then the subject is deemed to be a non-responder to beta-blocker treatment for heart failure.

In another aspect, the invention relates to a method of detecting single nucleotide polymorphisms (SNPs) relevant to the treatment of heart failure with a beta-blocker in a white subject of European ancestry/descent with heart failure, said method comprising: obtaining a biological sample from the subject; identifying whether at least twenty from a pool of at least 44 specific single nucleotide polymorphisms (SNPs) from Table 1 is present in the biological sample from the subject and, optionally, calculating a polygenic response predictor (PRP) score; based on the presence of the top 20 of the 44 weighted specific SNPs from Table 3 and obtains a PRP score of 12 or less, indicates that the subject is a responder to beta-blocker treatment in a heart failure setting, and wherein the presence of an alternative allele in the top 20 of the 44 specific single nucleotide polymorphisms (SNPs) from Table 3 results in a PRP score of above 12, indicates that the subject is a non-responder to beta-blocker treatment for heart failure.
Similarly, upon genotyping of the subject's DNA, the subject of European descent which has heart failure. Obtains a PRP score of 68 or less based on the presence of the top 41 to 44 weighted specific SNPs from Table 3, indicates that the subject is a responder to beta-blocker treatment in a heart failure setting, and wherein the presence of an alternative allele in the top 41 to 44 specific single nucleotide polymorphisms (SNPs) from Table 3 results in a PRP score of above 68, indicates that the subject is a non-responder to beta-blocker treatment for heart failure.

DETAILED DESCRIPTION

Figure 1:
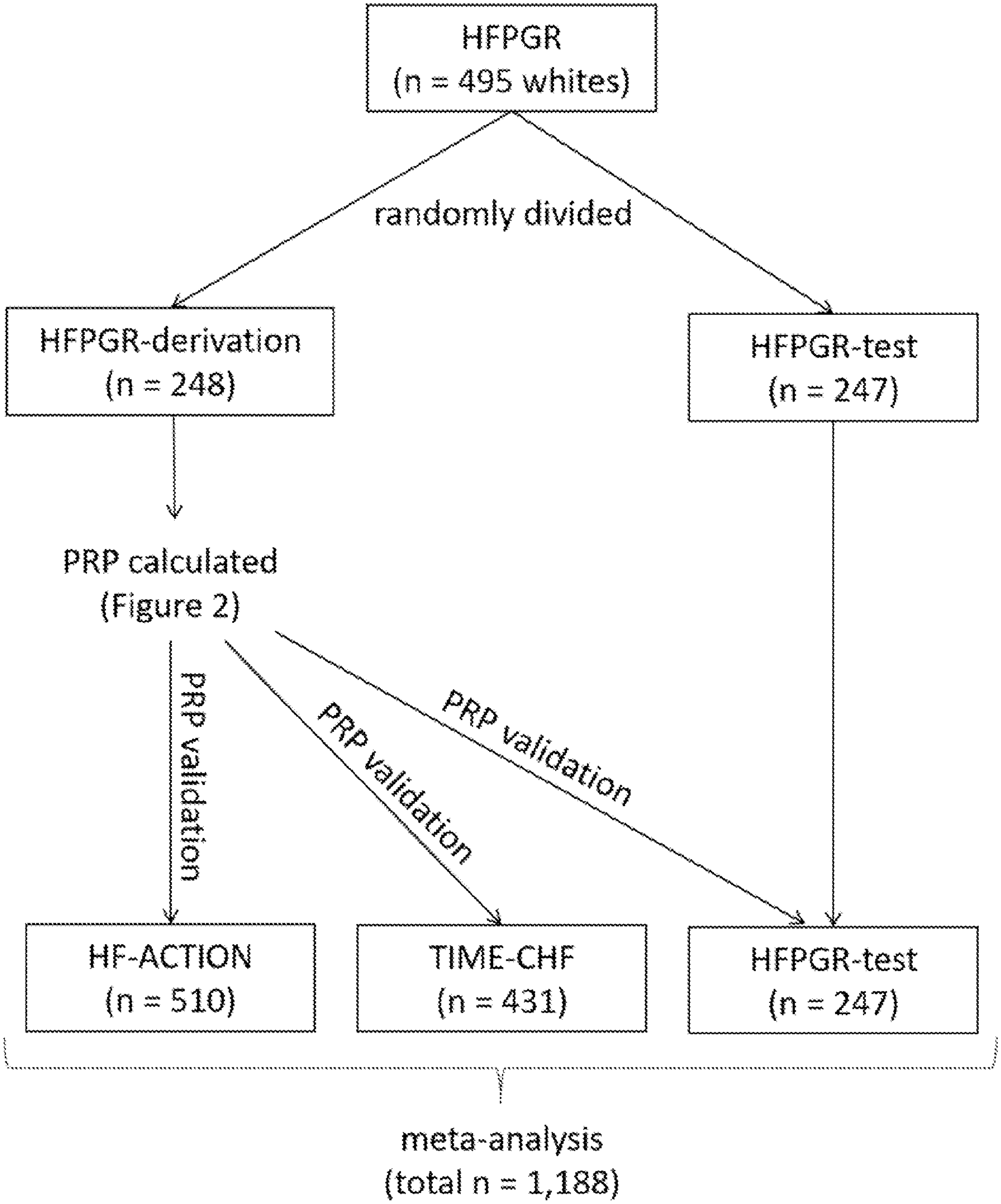
FIG. 1. depicts a schematic illustrating the use of the three datasets for polygenic response predictor (PRP) derivation and validation. HF-ACTION=the Heart Failure: A Controlled Trial Investigating Outcomes of Exercise Training; (37) HFPGR=Henry Ford Pharmacogenomic Registry (35); TIME-CHF=the Trial of Intensified vs Standard Medical Therapy in Elderly Patients With Congestive Heart Failure (36); PRP=polygenic response predictor.

The present disclosure provides various exemplary embodiments of systems and methods for applying multi-modal modeling techniques to make precise beta-blocker efficacy predictions for heart failure individuals who are white (Caucasian) and of European ancestry/descent and identifying actionable polygenic response predictor score for the same. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to,
or coupled to the other element or there are one or more intervening elements between the one element and the other element. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., Molecular Cloning: A Laboratory Manual (Third ed., Cold Spring Harbor Laboratory Press, Cold Spring Harbor, N.Y. 2000). The nomenclatures utilized in connection with, and the laboratory procedures and techniques described herein are those well-known and commonly used in the art.

Definitions

Unless otherwise defined, all technical terms used herein have the same meaning as commonly understood by one of ordinary skill in the art to which this invention belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by about 10%, 5%, or 1%, including increments therein.

As used herein, the term "individual" refers to a human individual, unless otherwise specified.

As used herein, the term "heart failure" as used herein relates to a condition which can be characterized as Doctors usually classify patients' heart failure according to the severity of their symptoms. The table below describes the most commonly used classification system, the New York Heart Association (NYHA) Functional Classification 1. It places patients in one of four categories based on how much they are limited during physical activity. NYHA Class I: No limitation of physical activity. Ordinary physical activity does not cause undue fatigue, palpitation, dyspnea (shortness of breath).

NYHA Class II: Slight limitation of physical activity. Comfortable at rest. Ordinary physical activity results in fatigue, palpitation, dyspnea (shortness of breath).

NYHA Class III: Marked limitation of physical activity. Comfortable at rest. Less than ordinary activity causes fatigue, palpitation, or dyspnea.

NYHA Class IV: Unable to carry on any physical activity without discomfort. Symptoms of heart failure at rest. If any physical activity is undertaken, discomfort increases.

In some embodiments, each category of heart failure under the functional NYHA classification system may also be accompanied by an objective assessment of the particular severity of the heart failure, for example, Class A: No objective evidence of cardiovascular disease. No symptoms and no limitation in ordinary physical activity. Class B: Objective evidence of minimal cardiovascular disease. Mild symptoms and slight limitation during ordinary activity. Comfortable at rest. Class C: Objective evidence of moderately severe cardiovascular disease. Marked limitation in activity due to symptoms, even during less-than-ordinary activity. Comfortable only at rest. Class D: Objective evidence of severe cardiovascular disease. Severe limitations. Experiences symptoms even while at rest.

For Example: A patient with minimal or no symptoms but a large pressure gradient across the aortic valve or severe obstruction of the left main coronary artery is classified: Function Capacity I, Objective Assessment D. In another example, a patient with severe anginal syndrome but angiographically normal coronary arteries is classified: Functional Capacity IV, Objective Assessment A. These functional classifications and objective assessments are known in the art and have been described in: Dolgin M, Association NYH, Fox A C, Gorlin R, Levin R I, New York Heart Association. Criteria Committee. Nomenclature and criteria for diagnosis of diseases of the heart and great vessels. 9th ed. Boston, MA: Lippincott Williams and Wilkins; Mar. 1, 1994; and Criteria Committee, New York Heart Association, Inc. Diseases of the Heart and Blood Vessels. Nomenclature and Criteria for diagnosis, 6th edition Boston, Little, Brown and Co. 1964, p 114, the disclosures of which are incorporated herein by reference in their entireties.

As used herein, "a symptom associated with heart failure" includes, but is not limited to, one or more symptoms associated with NYHA functional classifications I-IV as described herein. In some embodiments, symptoms associated with heart failure may include a symptom such as fatigue, palpitation, or dyspnea (shortness of breath).

The term "allele" refers to one of two or more different nucleotide sequences that occur or are encoded at a specific locus, or two or more different polypeptide sequences encoded by such a locus. For example, a first allele can occur on one chromosome, while a second allele occurs on a second homologous chromosome, e.g., as occurs for different chromosomes of a heterozygous individual, or between different homozygous or heterozygous individuals in a population. One example of a polymorphism is a "single nucleotide polymorphism" (SNP), which is a polymorphism at a single nucleotide position in a genome (the nucleotide at the specified position varies between individuals or populations).

An allele "positively" correlates with a trait when it is linked to it and when presence of the allele is an indicator that the trait or trait form will occur in an individual comprising the allele. An allele negatively correlates with a trait when it is linked to it and when presence of the allele is an indicator that a trait or trait form will not occur in an individual comprising the allele.

A marker polymorphism or allele is "correlated" or "associated" with a specified phenotype (e.g. beta-blocker responder, etc.) when it can be statistically linked (positively or negatively) to the phenotype. That is, the specified polymorphism occurs more commonly in a case population (e.g., beta-blocker responders versus non-responders) than in a control population (e.g., individuals that do not have heart failure). This correlation is often inferred as being causal in nature, but it need not be—simple genetic linkage to (association with) a locus for a trait that underlies the phenotype is sufficient for correlation/association to occur.

A "favorable allele" is an allele at a particular locus that positively correlates with a desirable phenotype, e.g., beta-blocker responsiveness (or responder to beta-blocker treatment in a heart failure patient). A favorable allele of a linked marker is a marker allele that segregates with the favorable allele. A favorable allelic form of a chromosome segment is a chromosome segment that includes a nucleotide sequence that positively correlates with the desired phenotype, or that negatively correlates with the unfavorable phenotype at one or more genetic loci physically located on the chromosome segment.

An "unfavorable allele" is an allele at a particular locus that negatively correlates with a desirable phenotype, or that correlates positively with an undesirable phenotype, e.g., positive correlation refractory or resistant to beta-blocker treatment in a heart failure setting. An unfavorable allele of a linked marker is a marker allele that segregates with the unfavorable allele. An unfavorable allelic form of a chromosome segment is a chromosome segment that includes a nucleotide sequence that negatively correlates with the desired phenotype, or positively correlates with the undesirable phenotype at one or more genetic loci physically located on the chromosome segment.

A "risk allele" is an allele that positively correlates with the risk of not being a beta-blocker responder, or risk of being a non-responder to beta-blocker administration, i.e. indicates that an individual has an increased likelihood to being a beta-blocker non-responder.

A beta-blocker or beta blockers drug (also referred to herein in the present disclosure as "BB"), also known as beta-adrenergic blocking agents, are medications that reduce your blood pressure. Beta blockers work by blocking the effects of the hormone epinephrine, also known as adrenaline. Beta blockers cause the heart to beat more slowly and with less force, which lowers blood pressure. Beta blockers can also veins and arteries to dilate and to improve blood flow. Examples of beta-blocker treatments or medications may include, but not limited to: acebutolol (SECTRAL), atenolol (TENORMIN), betaxolol (KERLONE), betaxolol (BETOPIC S), bisoprolol fumarate (ZEBATA), carteolol (CARTROL), carvedilol (COREG), esmolol (BREVIBLOC), labetalol (TRANDATE [NORMODYNE]), metoprolol (LOPRESSOR, TOPROL XL), nadolol (CORGARD), nebivolol (BYSTOLIC), penbutolol (LEVATOL), pindolol (VISKEN), propranolol (HEMANGEOL, INDERAL LA, INDERALXL, INNOPRAN XL), sotalol (BETAPACE, SORINE), timolol (BLOCADREN), and/or timolol ophthalmic solution (TIMOPTIC, BETIMOL, ISTALOL), or any United States Food and Drug Administration (FDA) approved beta-blocker for the treatment of hypertension and heart failure in Caucasian or white subjects of European ancestry/descent.

As used herein, the term "diagnosis" refers to methods by which a determination can be made as to whether a subject is likely to be suffering from a given disease or condition, including but not limited symptoms associated with the disease or condition. The skilled artisan often makes a diagnosis on the basis of one or more diagnostic indicators, e.g., a marker, the presence, absence, amount, or change in amount of which is indicative of the presence, severity, or absence of the disease or condition. Other diagnostic indicators can include patient history; physical symptoms, e.g., a reduced cardiac ejection fraction of 70% or less; phenotype; genotype; or environmental or heredity factors. A skilled artisan will understand that the term "diagnosis" refers to an increased probability that certain course or outcome will occur; that is, that a course or outcome is more likely to occur in a patient exhibiting a given characteristic, e.g., the presence or level of a diagnostic indicator, when compared to individuals not exhibiting the characteristic. Diagnostic methods of the present disclosure can be used independently, or in combination with other diagnosing methods, to determine whether a course or outcome is more likely to occur in a patient exhibiting a given characteristic.

The term "extract" used in the present invention means to obtain data to determine a marker (e.g., a genetic marker such as SNP or an image marker such as a pixel) at a specific time in a predetermined period. With respect to image data, the term may include two-dimensional or three-dimensional representations.

The term "two-dimensional" or "three-dimensional" in the context of image data means expression of the image in terms of the coordinate positions by using two coordinates or three coordinates. A "two-dimensional image" in the present invention includes a cross section image which is acquired by imaging a certain cross section, as well as a two-dimensional projected image which is acquired by projecting three-dimensional image data obtained by imaging a subject.

As used herein, the term "marker" refers to a characteristic that can be objectively measured as an indicator of normal biological processes, pathogenic processes (e.g., heart failure) or a response to a heart-failure intervention (i.e. heart failure medications), e.g., treatment with an Angiotensin-Converting Enzyme (ACE) Inhibitor (e.g., Captopril (CAPOTEN), Enalapril (VASOTEC), Fosinopril (MONOPRIL), Lisinopril (PRINIVIL, ZESTRIL), Perindopril (ACEON), Quinapril (ACCUPRIL), Ramipril (ALTACE), and Trandolapril (MAVIK); an angiotensin II receptor blocker, (e.g. Candesartan (ATACAND), Losartan (COZAAR), or Valsartan (DIOVAN); an Angiotensin-Receptor Neprilysin Inhibitors (ARNis) (e.g. Sacubitril/valsartan); an Ir Channel Blocker (or inhibitor) (e.g. Ivabradine (CORLANOR)); a beta-blocker (Beta-Adrenergic Blocking Agent) (e.g. Bisoprolol (ZEBETA), Metoprolol succinate (TOPROL XL), Carvedilol (COREG), Carvedilol CR (COREG CR); or an Aldosterone Antagonist (e.g. Spironolactone (ALDACTONE), and Eplerenone (INSPRA); a Hydralazine and isosorbide dinitrate agent (specifically benefits African-Americans with heart failure) (e.g. Hydralazine and isosorbide dinitrate (combination drug)—(Bidil); a Diuretic (e.g. Furosemide (LASIX), Bumetanide (BUMEX), Torsemide (DEMADEX), Chlorothiazide (DIURIL), Amiloride (MIDAMOR), Chlorthalidone (HYGROTON), Hydrochlorothiazide or HCTZ (ESIDRIX, HYDRODIURIL), Indapamide (LOZOL), Metolazone (ZAROXOLYN), and Triamterene (DYRENIUM). Representative types of markers include, for example, genomic markers, structural markers, actionable markers, epidemiological markers, or a combination thereof. Genomic markers include, e.g., molecular changes in the structure (e.g., sequence) or number of the genetic feature, comprising, e.g., polymorphisms, gene mutations, gene duplications, or a plurality of differences, such as somatic alterations in DNA, copy number variations, tandem repeats, or a combination thereof. Structural markers include image data of the tissue or region of interest, e.g. myocardium.

DNA (deoxyribonucleic acid) is a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides.
Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

The term "genetic feature" refers to a property of a genome or an expression product thereof (e.g., an mRNA transcriptome or a polypeptide proteome). The term encompasses positions in a genome (e.g., chromosome) as well as changes therein (e.g., a variant genome). Preferably, the genetic feature includes variant nucleic acids, e.g., mutations, SNPs, CNVs, STRs, or a combination thereof compared to a reference sample. Particularly, the variations are in the coding region of the nucleic acids, especially in the exomes. The variant nucleic acids preferably encode for an altered protein product, e.g., a protein product whose amino acid composition or length or both is different from a reference (e.g., wild-type) polypeptide product. "Genetic features" can refer to a genome region with some annotated function (e.g., a gene, protein coding sequence, mRNA, tRNA, rRNA, repeat sequence, inverted repeat, miRNA, siRNA, etc.) or a genetic/genomic variant (e.g., single nucleotide polymorphism/variant, insertion/deletion sequence, copy number variation, inversion, etc.) which denotes a single or a grouping of genes (in DNA or RNA) that have undergone changes as referenced against a particular species or sub-populations within a particular species due to mutations, recombination/crossover or genetic drift.

As used herein, the term "single nucleotide polymorphism" or "single nucleotide variation" ("SNP" or "SNV") in reference to a mutation refers to a difference of at least one nucleotide in a sequence in comparison to another sequence. The term "copy number variation" or "CNV" refers to a comparative numerical change in the presence or absence/gain or loss, of gene fragments having the same nucleotide sequence.

The term "indel" as used herein, and generally in the art, refers to a location on a genome where one or more bases are present in one allele, with no bases present in another allele. Insertions or deletions are distinct from an evolutionary point of view, but during analysis such as described herein, they are often not distinguished as an insertion in one allele is equivalent to a deletion in the other allele. Thus the term indel is to refer to the location of the insertion/deletion between two alleles.

"Structural variants" involve changes in some parts of the chromosomes instead of changes in the number of chromosomes or sets of chromosomes in the genome. There are four common types of mutations which result in structural variants: deletions and insertions, for example duplications (involving a change in the amount of DNA in a chromosome, loss and gain of genetic material, respectively), inversions (involving a change in the arrangement of a chromosomal segment) and translocations (involving a change in the location of a chromosomal segment which can give rise to gene fusions). In the present invention, the term "structural variant" includes loss of genetic material, a gain of genetic material, a translocation, a gene fusion and combinations thereof.

As used herein, the term "variation" refers to a change or deviation. In reference to nucleic acid, a variation refers to a difference(s) or a change(s) between DNA nucleotide sequences, including differences in copy number (CNVs). This actual difference in nucleotides between DNA sequences may be an SNP, and/or a change in a DNA sequence, e.g., fusion, deletion, addition, repeats, etc., observed when a sequence is compared to a reference, such as, e.g., germline DNA (gDNA) or a reference human genome HG38 sequence. Information on short genetic variations can be obtained using NCBI's SNP database (dbSNP) using Ref SNP (rs) numbers. Information on large structural variations, e.g., insertions, deletions, duplications, inversions, mobile elements, and translocations can be obtained using NCBI's variation database (dbVar) using an NCBI (nsv) or EBI (esv) reference number.

A variation can be "rare" "low frequency" or "common." Generally, common variants have a minor allele frequency (MAF) that is greater than 5% and usually exert a very weak effect or association with the phenotype (e.g., a disease) of interest. Low-frequency variants typically have a MAF of about 1%-5%. In contrast, rare variants typically have a MAF<1%, or even <0.2% and may exert a small to modest effect or association with the phenotype (e.g., a disease) of interest.

The term "polygenic" as used herein refers to association with multiple genetic features, e.g., mutations, polymorphisms, CNVs, indels, duplications, or translocations, in more than a single gene. Polygenic traits usually include complex diseases, disorders, syndromes that are caused by dysfunction in two or more genes and may also include non-pathological characteristics associated with the interaction of two or more genes. The term is contrasted with "monogenic" which refers to association of a trait, normal or pathological, with a single genetic feature. Monogenic traits usually include diseases caused by a dysfunction in a single gene (e.g., sickle cell anemia). Monogenic traits also include non-pathological characteristics (e.g., presence or absence of cell surface molecules on a specific cell type).

As used herein, the term "missense mutation" refers to a change in the DNA sequence that changes a codon in the MRNA that is normally translated as one amino acid into a codon that is translated as a different amino acid. Some but not all missense mutations result in a non-functional gene-product. Some missense mutations may also result in a gain of function. A selection method may be used to find those missense mutations that substantially affect the protein function.

As used herein, the term "loss-of-function (LoF) mutation" or "inactivating mutation" refers to mutations which result in partial or complete inactivation of the gene product. The term includes "amorphic mutation" which refers to instances wherein an allele has a complete loss of function (null allele). In contrast, "gain-of-function (GoF) mutations" or "activating mutations" refers to mutations which enhance activity of the protein product or which result in a wholly different (and abnormal) activity of the protein.

A "locus" (plural "loci") corresponds to an identified location in a genome, and can span a single base or a sequential series of multiple bases. A locus is typically identified by using an identifier value or a range of identifier values with respect to a reference genome and/or a chromosome thereof. A "heterozygous locus" (also referred to as a "bet") is a locus in a genome, where the two copies of a chromosome do not have the same sequence. These different sequences at a locus are called "alleles". A bet can be a single-nucleotide polymorphism (SNP)
if the reference genome location has two alleles that differ by a single base. A "het" can also be a reference genome location where there is an insertion or a deletion (collectively referred to as an "indel") of one or more nucleotides or one or more tandem repeats. A "homozygous locus" is a locus in a reference or a baseline genome, where the two copies of a chromosome have the same allele. "Haplotype" of a chromosome refers to whether the chromosome is present once or twice in a genome. A "region" in a genome may include one or more loci.

As used herein, the term "germline DNA" or "gDNA" refers to DNA isolated or extracted from a subject's germline cells, e.g., peripheral mononuclear blood cells, including lymphocytes that are in turn obtained from circulating blood.

The term "control," as used herein, refers to a reference for a test sample, such as control DNA isolated from peripheral mononuclear blood cells and lymphocytes, where these cells are not cancer cells, and the like. A "reference sample," as used herein, refers to a sample of tissue or cardiomyocyte cells that may or may not have been derived from a heart failure heart that are used for comparisons. Thus a "reference" sample thereby provides a basis to which another sample, for example plasma sample containing markers, e.g., exomic markers can be compared. In contrast, a "test sample" refers to a sample compared to a reference sample or control sample. In some embodiments, the reference sample or control may comprise a reference assembly.

When trade names are used herein, applicants intend to independently include the trade name product formulation, the generic drug, and the active pharmaceutical ingredient(s) of the trade name product.

The term "reference assembly" refers to a digital nucleic acid sequence database, such as the human genome (HG38) database containing HG38 assembly sequences. The gateway can be accessed through the Human (*Homo sapiens*) University of California Santa Cruz Genome Browser Gateway via the web at genome.ucsc.edu. Alternately, the reference assembly may refer to the Genome Reference Consortium's Human Genomic Assembly (Build #38; Assembled: June, 2017), which is accessible on the internet via the U.S. NCBI website.

As used herein, the term "sequencing" or "sequence" as a verb refers to a process whereby the nucleotide sequence of DNA, or order of nucleotides, is determined, such as a nucleotide order AGTCC, etc. The term "sequence" as a noun refers to the actual nucleotide sequence obtained from sequencing; for example, DNA having the sequence AGTCC. Wherein the "sequence" is provided and/or received in digital form, e.g., in a disk or remotely via a server, "sequencing" may refer to a collection of DNA that is propagated, manipulated and/or analyzed using the methods and/or systems of the disclosure.

The term "sequencing run" refers to any step or portion of a sequencing experiment performed to determine some information relating to at least one biomolecule (e.g., nucleic acid molecule).

The term "whole genome sequencing" or "\VGS" refers to a laboratory process that determines the DNA sequence of each DNA strand in a sample. The resulting sequences may be referred to as "raw sequencing data" or "read." As used herein, a read is a "mappable" read when the sequence has similarity to a region of a reference chromosomal DNA sequence.
The term "mappable" may refer to areas that show similarity to and thus "mapped" to a reference sequence, for example, a segment of cfDNA showing similarity to reference sequence in a database, for example, cfDNA having a high percentage of similarity to human chromosomal region 8q248q24.3 in the human genome (HG38) database, is a "mappable read."

In addition to "WGS," the genomic compendiums may be obtained using targeted sequencing. In contrast to WGS, the term "targeted sequencing," as used herein, refers to a laboratory process that determines the DNA sequence of chosen DNA loci or genes in a sample, for example sequencing a chosen group of cancer-related genes or markers (e.g., a target). In this context, the term "target sequence" herein refers to a selected target polynucleotide, e.g., a sequence present in a cfDNA molecule, whose presence, amount, and/or nucleotide sequence, or changes therein, are desired to be determined. Target sequences are interrogated for the presence or absence of a somatic mutation. The target polynucleotide can be a region of gene associated with a disease, e.g., cancer. In some embodiments, the region is an exon.

As used herein the term "whole exome sequencing" refers to selective sequencing of coding regions of the DNA genome. The targeted exome is usually the portion of the DNA that translate into proteins, however regions of the exome that do not translate into proteins may also be included within the sequence. The robust approach to sequencing the complete coding region (exome) can be clinically relevant in genetic diagnosis due to the current understanding of functional consequences in sequence variation, by identifying the functional variation that is responsible for both Mendelian and common diseases without the high costs associated with a high coverage whole-genome sequencing while maintaining high coverage in sequence depth. See, Ng et al., Nature 461, 272-276, 2009 and Choi et al., PNAS USA 106, 19096-19101, 2009.

As used herein the term "whole transcriptome sequencing" refers to determining the expression of all RNA molecules including messenger RNA (mRNA), ribosomal RNA (rRNA), transfer RNA (tRNA), and non-coding RNA. Whole transcriptome sequencing can be done with a variety of platforms for example, the GENOME ANALYZER (ILLUMINA, INC., San Diego, Calif, USA) and the SOLID™ Sequencing System (LIFE TECHNOLOGIES, Carlsbad, Calif, USA). However, any platform useful for whole transcriptome sequencing may be used. The term "RNA-Seq" or "transcriptome sequencing" refers to sequencing performed on RNA (or cDNA) instead of DNA, where typically, the primary goal is to measure expression levels, detect fusion transcripts, alternative splicing, and other genomic alterations that can be better assessed from RNA RNA-Seq includes whole transcriptome sequencing as well as target specific sequencing.

The phrase "next generation sequencing" (NGS) refers to sequencing technologies having increased throughput as compared to traditional Sanger- and capillary electrophoresis-based approaches, for example with the ability to generate hundreds of thousands of relatively small sequence reads at a time. Various aspects and embodiments of the systems and methods disclosed herein employ the use of NGS technologies. Some examples of next generation sequencing techniques include, but are not limited to, sequencing by synthesis, sequencing by ligation, and sequencing by hybridization. More specifically, the MISEQ, HISEQ and NEXT SEQ Systems of ILLUMINA and the Personal Genome Machine (PGM) and SOLiD Sequencing System of LIFE TECHNOLOGIES, provide massively parallel sequencing of whole or targeted genomes. The SOLiD System and associated workflows, protocols, chemistries, etc. are described in more detail in WO 2006/084132 and U.S. Pat. Nos. 8,536,099 and 8,934,098, entirety of each of these applications being incorporated herein by reference thereto.

Genomic variants can be identified using a variety of techniques, including, but not limited to: array-based methods (e.g., DNA microarrays, etc.), real-time/digital/quantitative PCR instrument methods and whole or targeted nucleic acid sequencing systems (e.g., NGS systems, Capillary Electrophoresis systems, etc.). With nucleic acid sequencing, coverage data can be available at single base resolution.

As used herein, the phrase "genomic region" or "genome region" denotes a region within a genome that can be defined in one of three ways—as (1) by a tagging SNP region, (2) an explicitly defined genomic region, or (3) a list of genes. For example, (1) genomic regions can be defined around any SNPs listed in HapMap. That is, a region can be defined around any named SNP using linkage disequilibrium (LD) properties. Specifically, the SNP region can start at the SJ>location and proceed to the furthest neighboring SNPs in the 3' and 5' direction in LD (r2>0.5). It can then proceed outwards in each direction to the nearest recombination hotspot. If no genes are in that region—the region can be expanded a set number of bases (i.e., 250 kb or more) in either direction. (2) Regions can also be explicitly defined. In that case indicate the Human Genome Assembly (e.g., hgl7, hgl8, etc.) that your regions are defined in. Then describe the region with four fields in order: a unique word identifier, the chromosome that the region is on, the start position (base pairs), and the end position (base pairs). (3) Regions can also be defined as a gene list. In this case for each line enter a unique word identifier, followed by the term GID. Then list each gene separated by spaces using their Entrez ID.

As used herein, the phrase "linked" refers to a region of a chromosome that is shared more frequently in family members affected by a particular disease, than expected by chance, thereby indicating that the gene or genes within the linked chromosome region contain or are associated with a marker or functional polymorphism that is correlated to the presence of, or risk of, disease. Once linkage is established, association studies (linkage disequilibrium) can be used to narrow the region of interest or to identify the risk conferring gene for heart failure in white European descended human subjects.

As used herein, the phrase "associated with" when used to refer to a marker or functional polymorphism and a particular gene means that the functional polymorphism is either within the indicated gene, or in a different physically adjacent gene on that chromosome. In general, such a physically adjacent gene is on the same chromosome and within 2 or 3 centimorgans of the named gene (i.e., within about 3 million base pairs of the named gene).

As used herein, the term "actionable risk features" includes phenotypic, lifestyle, and environmental features that can be modified. Representative examples include, but are not limited to, alcohol use (action: lower intake), obesity (action: reduce caloric intake), diabetes (action: lower sugar intake; take diabetes medication), high blood pressure (action: lower salt intake; take antihypertensive medication), high cholesterol (action: lower cholesteric food intake; take drugs such as statins), vitamin B12 (action: consume B12-rich foods), depression (action: take antidepressants), head injuries (action: reduce contact sports), and lack of physical activity (action: increase exercise); preferably, high BMI, alcohol abuse, high cortisol, low vitamin B12, high medium-chain triglycerides (MCTs), elevated bilirubin, high triglyceride level, high serum uric acid, high diastolic blood pressure (BP), and high systolic BP.

As used herein, the term "epidemiological features" include population-specific parameters of a disease of interest. The term includes, prevalence, incidence, person-time at risk, duration of disease, survival, mortality, including measures of effect (e.g., risk ratio, rate ratio, odds ratio) in a population or sub-population of subjects.

As used herein, the phrase "medical imaging techniques", "medical imaging methods" or "medical imaging systems" can denote techniques or processes for obtaining visual representations of the interior of an individual's body for clinical analysis and medical intervention, as well as visual representation of the function of some organs or tissues. Within these visual representations various imaging features can be identified and characterized to provide a structural basis for diagnosing and treating various types of diseases (e.g., cardiovascular disease, cerebrovascular disease, etc). Examples of medical imaging techniques can include, but are not limited to, echo cardiography, x-ray radiography, magnetic resonance imaging, ultrasound, positron emission tomography (PET), computed tomography (CT), etc.

The present disclosure provides methods for the treatment of heart failure in subjects that are predisposed to genetically benefiting from beta-blocker therapy, and methods for determining such subjects. In one embodiment, the present disclosure provides a method of treating a subject suffering from heart failure, comprising: a) obtaining a nucleic acid sample from the subject; b) detecting in the nucleic acid sample of the subject the presence or absence of a plurality of single nucleotide polymorphisms (SNPs) required for the determination of a beta-blocker polygenic response predictor (BB-PRP) indicative of the likelihood of survival benefit of beta-blocker treatment; c) identifying the subject as a: i) BB responder; or ii) BB non-responder; and d) administering treatment to the subject identified in step c(i), wherein the treatment comprises a beta-blocker drug.

In another related embodiment, the present disclosure provides a method of treating a subject suffering from heart failure, comprising: a) sequencing or genotyping a nucleic acid sample from the subject; b) detecting in the nucleic acid sample of the subject the presence or absence of a plurality of single nucleotide polymorphisms (SNPs) required for the determination of a beta-blocker polygenic response predictor (BB-PRP) indicative of the likelihood of survival benefit of beta-blocker treatment; c) identifying the subject as a: i) beta-blocker (BB) responder; or ii) BB non-responder; and d) administering treatment to the subject identified in step c(i), wherein the treatment comprises administering a beta-blocker drug to the subject identified in step c(i).

In another embodiment of the present disclosure, a method of treating a subject suffering from heart failure is provided, the method comprising the steps of: a) detecting in one or more cells of the subject, the presence or absence of a variance in each single nucleotide polymorphism (SNP) of Table 1, wherein the combination of the presence or absence of the variance for each SNP is indicative that said treatment will be effective, more effective, less effective or ineffective in the subject; and b) administering to the subject a treatment comprising a beta-blocker drug based on detection in step (a) indicative of an effective or more effective treatment for the subject.

Variable Response to Beta Adrenergic Antagonist Drugs (Beta-Blockers (BBs))

Beta adrenergic antagonist drugs (i.e., beta-blockers (BBs)) are a common medication approved for use for hypertension, angina, coronary artery disease and heart failure. They are the cornerstone of treatment for heart failure and provide a survival benefit in heart failure with reduced ejection fraction (ejection fraction <=40%). However, it is likely that not all patients derive benefit and some patients have adverse reactions to beta-blockers.

Other studies that have characterized beta-blockers and genetics that are single variants have been inconsistent and have not reached clinical utility. Others have focused on one or two genetic variants at a time (e.g., such as a single nucleotide polymorphism). Unlike other studies, the present disclosure provides an approach that provides a multi-site genetic score derived from unbiased, genome-wide data.

The present disclosure provides an approach that examines the entire genome and derives a robust polygenic score that indicates the likelihood of favorable response to beta-blocker based on a broad genomic profile (summarized into a score (a polygenic score)). The present disclosure also demonstrates methods that may be used to create and validate a polygenic score.

Polygenic Scores

Methods of Genotyping

The present disclosure provides methods of treatment and devices, systems and protocols operable to determine the polygenic response predictor related to beta-blocker drugs in the treatment of heart failure. Accordingly, the present disclosure involves detection and analysis of a large number of common genetic variants (e.g. SNPs) which can be used to calculate a beta-blocker polygenic response predictor score suitable for identifying individuals who are likely to benefit from beta-blocker therapy in the treatment of heart failure. Detection methods for detecting relevant alleles containing a SNP as provided in Table 3 include a variety of methods well known in the art, e.g., gene amplification technologies. For example, detection can include amplifying the polymorphism or a sequence associated therewith and detecting the resulting amplicon. This can include admixing an amplification primer or amplification primer pair with a nucleic acid template isolated from the organism or biological sample (e.g., comprising the SNP or other polymorphism), where the primer or primer pair is complementary or partially complementary to at least a portion of the target gene, or to a sequence proximal thereto. Amplification can be performed by DNA polymerization reaction (such as PCR, RT-PCR) comprising a polymerase and the template nucleic acid to generate the amplicon. The amplicon is detected by any available detection method, e.g., sequencing, hybridizing the amplicon to an array (or affixing the amplicon to an array and hybridizing probes to it), digesting the amplicon with a restriction enzyme (e.g., RFLP), real-time PCR analysis, single nucleotide extension, allele-specific hybridization, or the like. Genotyping can also be performed by other known techniques, such as using primer mass extension and MALDI-TOF mass spectrum (MS) analysis, such as the MassEXTEND methodology of Sequenom, San Diago, Calif.

Other forms of genotyping include whole genome sequencing which is generally known in the art. For example, whole genome sequencing and analysis can be performed using and the DNA sequencing methods in Table 1.

TABLE 1

Modem whole genome sequencing technologies useful in the present invention.

| Technology (manufacturer) | Sequencing chemistry | Platform | Read length (bp) | Throughput (Gb/h ran) | Best suited for: |
|---|---|---|---|---|---|
| Sanger | Dye terminator | ABI 3730xl | 700-900 | | De novo and metagenomics |
| 454 (ROCHE) | Pyrosequencing | GS FLX | 400-700 | 0.04 | De novo and metagenomics |
| | | GS JUNIOR | 400 | 0.004 | De novo and metagenomics |
| SOLEXA (ILLUMINA) | | GAIIX | 36-150 | 0.3 | Resequencing |
| | | HISEQ2000 | 36-100 | 2.9 | Resequencing |
| | Sequencing by synthesis with reversible terminators | MISEQ | 36-250 | 0.2 | Resequencing |
| SOLID (ABI) | Sequencing by ligation | 5500XL | 35-75 | 1 | Resequencing |
| HELISCOPE (HELICOS) | Sequencing by synthesis with virtual terminators | TSMS | 25-55 | 1 | Resequencing |
| ION TORRENT (LIFE TECHNOLOGIES) | Semiconductor sequencing | ION TORRENT PGM | 100-200 | 0.2 | Resequencing |
| | | ION PROTON SEQUENCER | 100-200 | 2.5 | Resequencing |
| PACBIO (PACIFIC BIOSCIENCE) | SMRT technology | PACBIORS | 250-10 000 | 0.1 | Genome structure and metagenomics |
| NANOPORE (OXFORD NANOPORE TECHNOLOGIES) | Ionic current sensing | GRIDION and MINION | 10 000-50 000 | — | De novo and genome structure |

Beta-Blocker Polygenic Response Predictor Score to Identify Responders and Non-Responders of Beta-Blocker administration in Heart Failure.

Methods for identifying white, Caucasian heart failure subjects of European ancestry/descent that are responders or non-responders to beta-blocker treatment may include the steps of:

a) obtaining a nucleic acid sample from the subject;
b) detecting in the nucleic acid sample of the subject the presence or absence of a plurality of single nucleotide polymorphisms (SNPs) required for the determination of a beta blocker polygenic response predictor (BB-PRP) indicative of the likelihood of survival benefit of beta blocker treatment.
c) identifying the subject as a:
   i) BB responder; or
   ii) BB non-responder; and
d) administering treatment to the subject identified in step c(i), wherein the treatment comprises a beta blocker drug.

In other examples, methods for identifying white, Caucasian heart failure subjects of European ancestry/descent that are responders or non-responders to beta-blocker treatment may include the steps of:

a) sequencing or genotyping a nucleic acid sample from the subject;
b) detecting in the nucleic acid sample of the subject the presence or absence of a plurality of single nucleotide polymorphisms (SNPs) required for the determination of a beta blocker polygenic response predictor (BB-PRP) indicative of the likelihood of survival benefit of beta blocker treatment;
c) identifying the subject as a:
   i) BB responder; or
   ii) BB non-responder; and
d) administering treatment to the subject identified in step c(i), wherein the treatment comprises a beta blocker drug.

In other examples, methods for identifying white, Caucasian heart failure subjects of European ancestry/descent that are responders or non-responders to beta-blocker treatment may include the steps of:

a) detecting in cells of the subject the presence or absence of a variance in each single nucleotide polymorphism (SNP) of Table ______, wherein the combination of the presence or absence of the variance for each SNP is indicative that said treatment will be effective, more effective, less effective or ineffective in the subject; and
b) administering to the subject a treatment comprising a beta blocker drug based on detection in step (a) indicative of an effective or more effective treatment for the subject.

The results for the determination of a PRP and validation results are discussed in the Examples below, show that heart failure subjects from the derivation dataset, i.e. European ancestry, white Caucasian heart failure patients with a low PRP score at or below 68 were hypothesized to be the BB responders in the validation datasets when 41 to 44 of the SNPs in Table 3 were calculated in accordance to Formula (I):

$$\text{score} = \sum_{j=1}^{x} w_j * SNP_j, \qquad \text{Formula (I)}$$

and patients with a high PRP (a PRP score above 68) were hypothesized to be BB non-responders in the validation datasets when 41 to 44 of the SJ\<'Ps in Table 3 were calculated in accordance to Formula (I). Accordingly, the PRP score is a useful tool to identify such patients for early intervention, and also to test candidate agents that might be effective in slowing down or inhibiting the progression of heart failure in the most vulnerable patient population.

The present disclosure provides enhanced early detection and treatment options to identify beta-blocker survival benefit in heart failure patients, e.g., by taking early preventative action, treating the patients with a raw PRP score of 12, or less (when the top 20 of the 44 SNPs in Table 3 are used in the calculation set forth in Formula (I)), or 68 or less, (when the top 41 to 44 SNPs in Table 3 are used in the calculation set forth in Formula (I)) are responders to beta-blocker treatment in the treatment of heart failure. In addition, the PRP score determined in accordance with the present disclosure can also assist in providing an indication of how likely it is that a heart failure patient of European ancestry/descent will respond to novel therapies related to beta adrenergic blockade. Accordingly, the present invention also enables the identification of a patient population for testing treatment options for preventing or slowing down the progression of an earlier stage of heart failure, e.g. NYHA Class 1 or II to NYHA Class III or IV.

Treatment of Heart Failure in Beta-Blocker Responders

In summary, the present disclosure provides a mechanism for calculating and determining a polygenic score for beta-blocker treatment survival benefit in heart failure patients of European ancestry. The PRP score was able to differentiate heart failure patients with a greatly enhanced beta-blocker-associated survival benefit from a larger group of heart failure patients that did not feature a statistically significant survival benefit. These findings challenge the "one size fits all" approach for beta-blocker treatment in heart failure (6) and are a step toward precision medicine for heart failure patients.

In one embodiment, the present disclosure provides a method for identifying and/or treating heart failure in a human subject of European ancestry/descent in need thereof, optionally having been diagnosed with heart failure, and/or as being at risk for developing heart failure comprising the steps:

(a) identifying a subject diagnosed with early stage or intermediate stage heart failure as being at risk for developing, intermediate or advanced heart failure, comprising:
(1) detecting in a biological sample from said subject the presence or absence of at least 20 SNPs of the 44 SNPs at independent loci selected from single nucleotide polymorphisms set forth in Table 3 associated with beta blocker efficacy in heart failure in subjects of European descent,
(2) calculating a polygenic response predictor (PRP) score according to Formula (I) and $$\text{score} = \sum_{j=1}^{x} w_j * SNP_j, \qquad \text{Formula (I)}$$

and (3) identifying the human subject as being a beta-blocker responder when the PRP score is less than 68 when the top 41-44 SNPs from Table 3 are used in the calculation of Formula (I), and wherein the subject is determined to be a non-responder if the PRP score is greater than 68 when the top 41-44 SNPs from Table 3 are used in the calculation of Formula (I), and (b) treating the human subject identified as being a beta-blocker responder with a therapeutically effective amount of a beta-blocker medicament comprising, selected from the group consisting of, or consisting of: acebutolol (Sectral), atenolol (Tenormin), betaxolol (Kerlone), betaxolol (Betoptic S), bisoprolol fumarate (Zebeta), carteolol (Cartrol), carvedilol (Coreg), esmolol (Brevibloc), labetalol (Trandate [Normodyne]), metoprolol (Lopressor, Toprol XL), nadolol (Corgard), nebivolol (Bystolic), penbutolol (Levatol), pindolol (Visken), propranolol (Hemangeol, Inderal LA, InderalXL, InnoPran XL), sotalol (Betapace, Sarine), timolol (Blocadren), and/or timolol ophthalmic solution (Timoptic, Betimol, Istalol).

Polygenic risk scores utilize genome-wide genotype data to estimate incident disease risk; this approach has not been applied to predict drug response in patients with known disease.

In some embodiments, the present disclosure provides a polygenic response predictor score to predict beta-blocker drug response in heart failure patients that are white and are of European ancestry/descent, based on an optimal cutoff. In some embodiments, the the PRP score of a responder is less than 68 when 41 to 44 SNPS of Table 3 are used in the calculation according to Formula (I), or the PRP score of a responder is less than 12 when the top 20 out of the 44 SNPS of Table 3 are used in the calculation according to Formula (I). If the calculated PRP score for the subject is greater than 68 when 41 to 44 SNPS of Table 3 are used in the calculation according to Formula (I), or when the PRP score is greater than 12 when the top 20 out of the 44 SNPS of Table 3 are used in the calculation according to Formula (I), then the subject is deemed a non-responder, and will have no statistical benefit with regards to amelioration of their heart failure by administering a beta-blocker to said non-responder heart failure subject. The score of the responder may also be calculated with any number of SNPs ranging from about 20 to about 44 SNPs, starting from the top of the list in descending order.

The PRP score can then be calculated using Formula (I), wherein if the BB-PRP score is less than:

(the No. of SNPs(ranging from the top 20-44 of Table 3)×41/(68), then the subject is a responder to beta-blocker treatment and can be used to treat heart failure successfully.

In some embodiments, the present disclosure provides a polygenic response predictor score for treatment in heart failure in white heart failure patients of European ancestry. In some embodiments, the present disclosure provides a beta-blocker PRP for treatment in heart failure with reduced ejection fraction (HFrEF). In some embodiments, the present disclosure provides a PRP for treatment in heart failure with midrange ejection fraction (EF). In some embodiments, the present disclosure provides a PRP for treatment in heart failure with HFrEF and with midrange EF. In some embodiments, the present disclosure provides a PRP for treatment in heart failure in a Caucasian or white, heart failure subject, of European ancestry/descent, with one or more of an left ventricular ejection fraction (LVEF) (EF<50%, an EF<40%, and an EF of 40-50%).

In some embodiments, the present disclosure provides a PRP based on a plurality of SNP loci. In some embodiments, the present disclosure provides a PRP based on the number of favorable alleles at each SNP site, weighted depending on impact of the particular loci.

The present disclosure illustrates methods by which a PRP may be created and validated. In some embodiments, a PRP may predict whether patients treated with a beta adrenergic antagonist drug (beta-blocker) will derive survival benefit. In some embodiments, the PRP may be derived from genome-wide data.

As disclosed herein, a genomic score may reproducibly predict the likelihood of an outcome (e.g., survival benefit) with respect to a treatment (e.g., beta-blockers) in a clinical context (e.g., heart failure). According to the present disclosure, an exemplary genomic score is a PRP that is based on weighted genotypes at loci across the genome, tabulated into a score. As an example, the present disclosure illustrates creation and validation of a genomic score by an approach that determines weighted genotypes at 44 loci across the genome, tabulated into a score. The approach disclosed herein provides a PRP that reproducibly predicts the likelihood of survival benefit of beta-blockers in the setting of heart failure. Such a PRP is also referred to herein as a beta-blocker polygenic response predictor (BB-PRP).

As disclosed herein, a genome-wide association study (GWAS) of beta-blockers (BB) in heart failure may be used to create a polygenic response predictor (PRP) for BB.

Applications

The present disclosure provides an approach to create and validate a PRP that can identify and/or predict likelihood of favorable response to treatment. Application of the PRP and methods described herein could provide for more efficient treatment; avoid unnecessary, wasteful and/or hazardous drug treatment; save cost and potential adverse events; and identify super-responders in new indications.

An exemplary PRP for predicting likelihood of survival benefit of beta-blockers in the setting of heart failure is disclosed. Accordingly, the present disclosure genetically identifies patients most likely to have a survival benefit with BB treatment and also genetically identifies patients that are unlikely to have a survival benefit from BB. Application of a PRP as disclosed herein would allow patients that are unlikely to benefit from treatment to avoid unbeneficial treatment and would also provide for extending the possible indications for beta-blockers by identifying 'responder' subgroups of the population.

Other types of heart failure such as midrange ejection fraction (LVEF: 40-50%) or heart failure with preserved ejection fraction (>50%), which currently do not have indications for beta-blocker, could benefit from application of a PRP score determination that can identify and define beta-blocker responders. By applying the PRP and approaches disclosed herein, new indications for existing treatments such as beta-blockers may be identified. Thus, the present disclosure provides for a treatment option with a companion diagnostic.

Further details of the invention are provided in the following non-limiting examples.

EXAMPLES

Example 1. Identification of Polygenic Response Predictor (PRP) for Beta-Blocker (BB) Survival Benefit in Heart Failure Patients of European Descent with LV Ejection Fraction <50%

The present example demonstrates methods that may be used to identify a polygenic response predictor (PRP) for treatment of disease (e.g., treatment of heart failure using Beta-blockers (BB)). The present example also demonstrates that a BB-PRP may identify patient subgroups that are BB responders versus non-responders.

Methods

Datasets and Overall Approach

Figure 5:
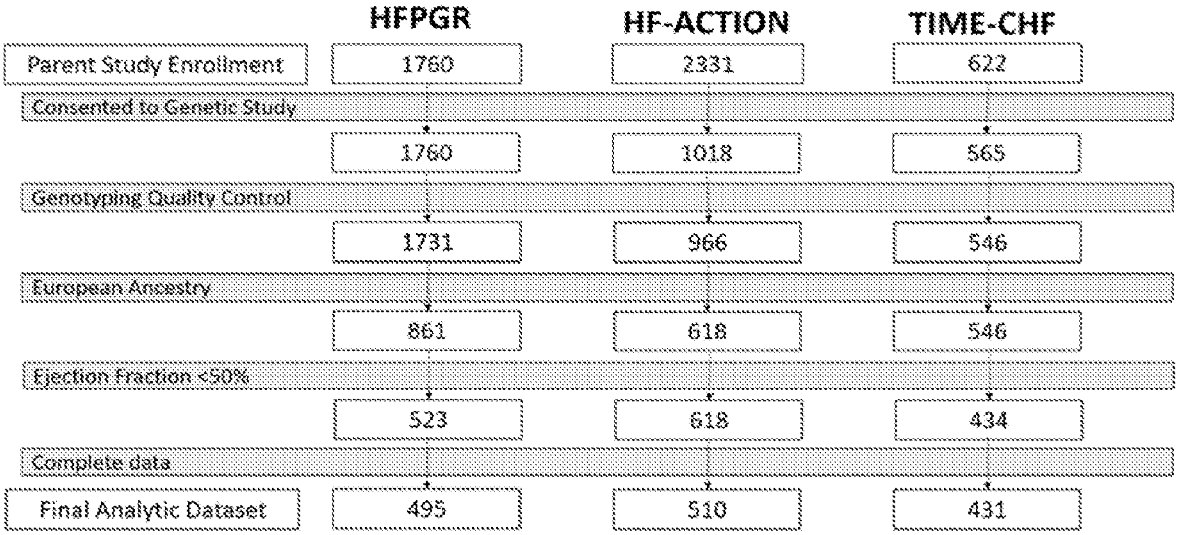
FIG. 5. depicts the number of patients enrolled in the studies described herein, and specified patient criteria observed in Example 1.

The current study was approved by the Henry Ford Hospital Institutional Review Board, and all participants provided written informed consent. Three datasets were used: the Henry Ford Heart Failure Pharmacogenomic registry (HFPGR); (35) the Trial of Intensified vs Standard Medical Therapy in Elderly Patients With Congestive Heart Failure (TIME-CHF); (36) and Heart Failure: A Controlled Trial Investigating Outcomes of Exercise Training (HF-ACTION). (37) The patient flow from parent study to final analytic cohorts is shown in the consort diagram FIG. 5. Only self-reported white patients were included in this analysis. The parent studies are described briefly below and in detail elsewhere, and each had institutional review board/ethics approval. (35-37) A diagram illustrating overall study design is presented in FIG. 1. We first created a derivation group upon which the PRP would be constructed, followed by testing in multiple independent datasets to test its performance. Since the HFPGR had the most granular drug-exposure data (derived from pharmacy claims and time-updating), it was randomly divided into two halves: one for derivation (n=248) and the other to be included in the validation (n=247). The PRP was derived solely in the derivation subset of HFPGR. Thus, the validation data included the remaining half of the HFPGR (n=247), TIME-CHF (n=431), and HF-ACTION (n=510) for a total of 1188 validation patients.

BB exposure was computed using two different methods depending on the cohort. For both HFPGR cohorts, BB exposure was calculated from pharmacy claims (i.e. drug actually dispensed to patient) and was updated over time, as previously described, (35, 38) and briefly summarized herein. For TIME-CHF and HF-ACTION BB exposure was calculated from the specific drug and dose at baseline, using the same dose-equivalence scheme as above but implemented without any updates over time and without information on medication dispensing (i.e. assumes patients were receiving the dose prescribed).

The HFPGR enrolled patients from October 2007 through March 2015 at Henry Ford Health System in Detroit, MI, USA. The overall goal of the HFPGR is to discover novel ways to better predict prognosis and response to HFrEF treatments. Patients aged 18 years or older were included if they had health insurance coverage, met the definition for heart failure as defined by the Framingham Heart Study, (39) and had at least one documented left ventricular ejection fraction (LVEF); a total of 1760 patients were enrolled. For the current analysis those with LVEF<50% and self-identified European ancestry were included (n=495). BB exposure was calculated from pharmacy claims and was updated over time, as previously described (35, 38).

TIME-CHF was a randomized controlled trial that took place at 15 centers in Switzerland and Germany from January 2003 to June 2008 that enrolled a total of 622 patients. The primary objective of the trial was to compare N-terminal pro-B-type natriuretic peptide (NTproBNP)-guided versus symptom-guided treatment for heart failure. To be included in the trial, individuals had to meet the following criteria: age>60 years, diagnosed with systolic heart failure, New York Heart Association (NYHA) class of II or greater, hospitalization for heart failure within the year prior to enrollment, and an NTproBNP level 2 times the upper limit of normal. For the current analysis, only patients consenting to participate in the genetic substudy with analyzable data and baseline LVEF<50% were included (n=431). BB exposure was calculated from the specific drug and dose at baseline, with dose standardization performed as previously described. (35, 38) Heart failure therapy guided by NTproBNP did not significantly affect the primary outcome.

HF-ACTION was a National Institute of Health funded randomized clinical trial that took place at 82 centers within the United States, Canada, and France from April 2003 through February 2007, enrolling a total of 2331 patients. The primary objective of the trial was to compare usual HFrEF care to usual HFrEF care plus exercise training, but it included a genetic sub-study. The trial included adult HFrEF patients with LVEF:S 35% and NYHA class II to IV symptoms despite optimal heart failure therapy for at least 6 weeks. BB exposure was calculated from the specific drug and dose at baseline, with dose standardization performed as previously described. (35) In primary analysis, exercise training resulted in non-significant reductions in the primary end point of all-cause mortality or hospitalizations although in the pre-specified adjusted analysis, the exercise intervention significantly reduced the composite primary outcome. We felt this did not justify the need to adjust for trial arm assignment when modeling all-cause mortality (the primary outcome for the current study). Only participants of the genetic sub-study with quality genetic array data, complete clinical data and self-identified as European ancestry were included in the current analysis (n=510).

Genotyping

Blood samples were collected, processed and stored at −70° C. DNA was extracted using standard methods. (40) Patients from all three studies were genotyped with the Axiom® Biobank array (Affymetrix, Santa Clara, CA). This array was designed to optimize genome-wide imputation, and it includes ~600,000 genetic variants with the following characteristics:

~300,000 genome-wide variants with minor allele frequencies >1%, ~250,000 low frequency (<1%) coding variants from global exome sequencing projects, and an additional ~50,000 variants for improved African ancestry coverage. All genotyping was performed at the University of Michigan genotyping core lab with standard quality checks performed. In brief, single nucleotide polymorphisms (SNPs) with a minor allele frequency <0.05, those not in Hardy-Weinberg equilibrium (HWE p<10-8), multi-allelic sites, and ambiguous SNPs were deleted from the analysis. Samples with sex inconsistencies (i.e., between patient report and genetically determined) or duplicate genotyping were removed. All datasets underwent imputation using the University of Michigan imputation server with Minimac3 (41) and using the cosmopolitan reference panel from the 1000 Genomes Project. (42) Imputed SNPs passing a quality threshold of r2>0.5 were included for analysis.

Polygenic Response Predictor (PRP) Construction

Figure 2:
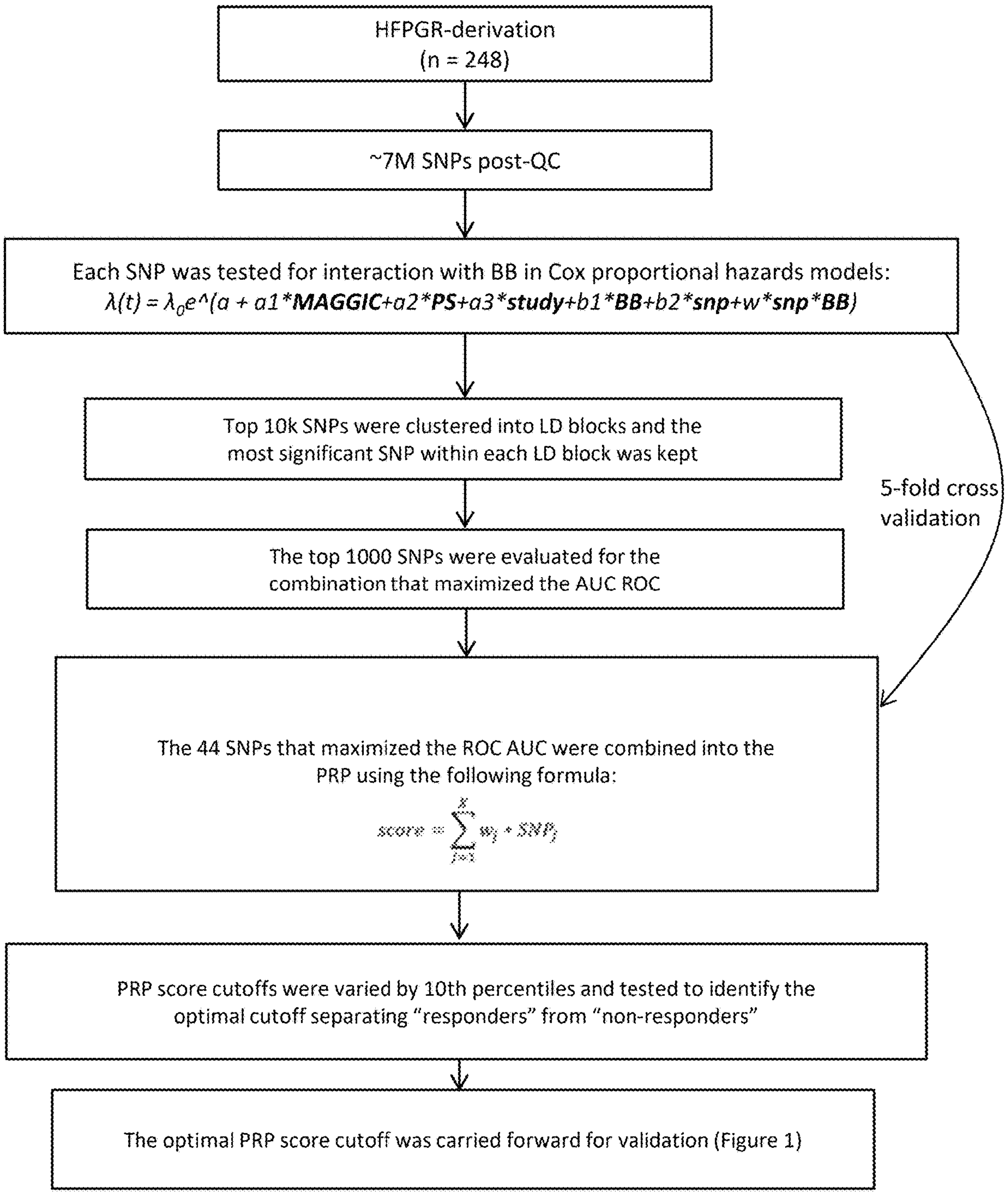
FIG. 2. depicts a schematic flow-chart and formulae for calculating the PRP. AUC=area under the curve; BB=Beta-blocker; LD=linkage disequilibrium; MAGGIC=Meta-Analysis Global Group in Chronic Heart Failure risk score; (43) PS=propensity score;
QC=quality control; ROC=receiver operating characteristic curve; SNP=single nucleotide polymorphism.
Figure 6:
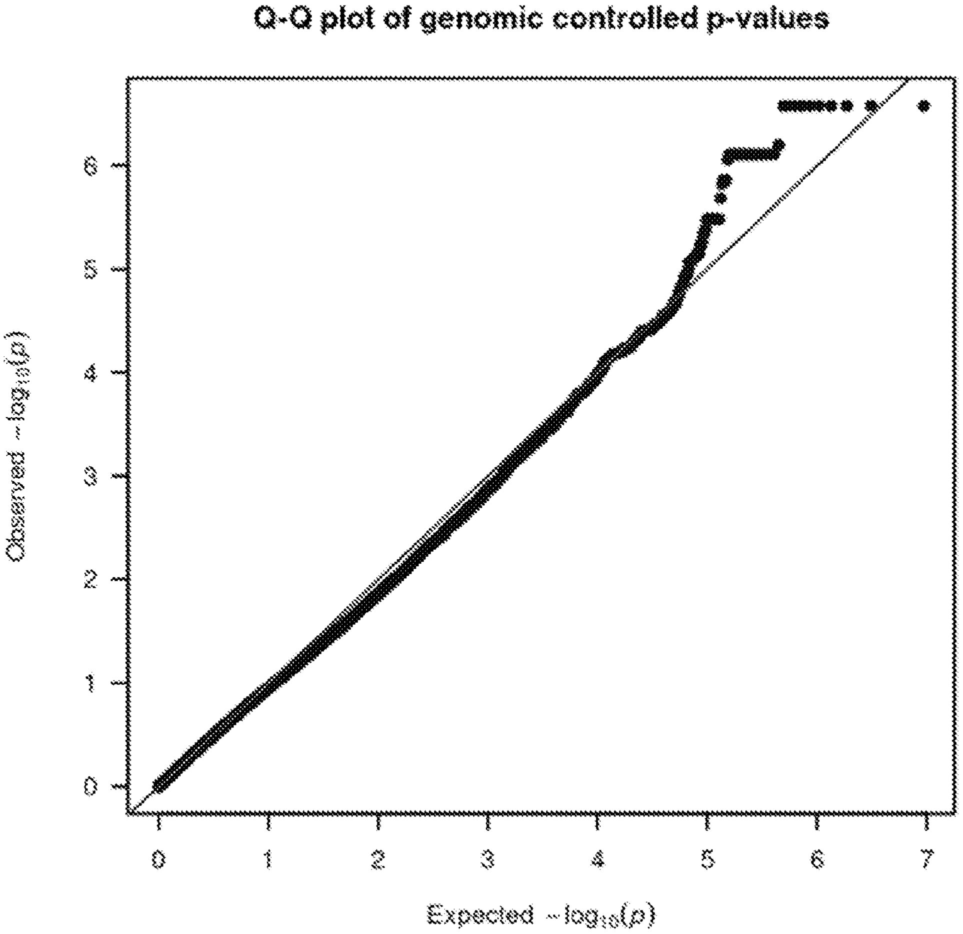
FIG. 6 depicts a Q-Q plot of the GWAS (Derivation cohort) in accordance with the examples provided in the present disclosure.

A combined SNP selection and multivariable data analysis strategy was formulated to derive the PRP based on a GWAS of the HFPGR-derivation cohort, summarized in FIG. 2. The primary outcome was time to all-cause mortality. This was modeled using Cox regression focusing in on the SNP-by-BB exposure multiplicative interaction term (SNP*BB) and including the main effects of BB exposure and SNP as covariates. An additional two covariates were also included in the model; to adjust for established clinical risk factors for death we include the MAGGIC score (calculated without BB as a contributing variable) (43) and to adjust for potential confounding by indication or treatment bias we included a BB propensity score (44) Thus the overall model was Death=MAGGIC+BBpropensity+BBexposure+SNP+SNP*BBexposure. The Q-Q plot of the GWAS result is shown in FIG. 6. BB propensity score was calculated using logistic regression of baseline characteristic variables with the resulting output separated into quartiles and used as an ordinal covariate. (45) BB exposure was implemented as a time-dependent covariate (this is specific to HFPGR). The SNPs were then ranked according to the p-value of SNP*BBexposure and the selected SNPs were pruned down to the most significant one within each linkage disequilibrium (LD) block, which was kept for subsequent analysis.

The PRP is a linear combination of SNPs, in which the SNP weights are determined by the estimated Cox regression coefficients in the original model (from the derivation cohort). To select the optimal number of SNPs to include, a series of scores were created using Cox models similar to the above (including MAGGIC, Propensity, BBexposure, SNP and SNP*BBexposure) but sequentially adding more and more SNP and SNP*BBexposure terms, starting with the most highly associated locus and then incrementally adding one SNP at a time, sorted according to the p-value. The SNPs were coded with an additive genetic model (0, 1, or 2 for minor allele count). These scores were tested using 5-fold cross-validation with the merge method (46) to select the optimal number of SNPs that would maximize the time-dependent AUC for I-year survival (estimated from the Cox model). The optimal set of SNPs (and the associated coefficients) were then used to build the final PRP.

To prepare for validation, the PRP was also dichotomized into "responder" and "non-responder" groups. The purpose of converting the continuous PRP into dichotomous categories was to facilitate clinical testing and future implementation of the PRP (i.e., to be able to identify sub-groups of patients where a specific therapeutic action is clearly defined). To accomplish this, we examined the BB survival benefit across a variety of score cutoff thresholds separating "responder" vs. "non-responders", the performance of each tested in the HFPGR derivation cohort. Performance was judged by examining the BB HRs for high and low PRP patients (separately) with the cutoff at increasing deciles of the PRP within the derivation cohort (i.e. trying the 10th percentile as the cutoff for low vs high, then 20th percentile, and so on). The HR in each PRP group and their separation was examined. Separation was best at 30th percentile in the derivation cohort and the raw score at this level was then carried forward throughout validation testing. For HF-ACTION, 3 SNPS of the PRP did not pass quality metrics, so these were excluded and the PRP was tabulated using the remaining 41 SNPs. The dichotomization point was recalculated using a matching (without those 3 SNPs) PRP in derivation set to identify the corresponding raw score, and this was used as the dichotomization point for HF-ACTION validation testing.

Statistical Analysis and PRP Validation

In validation, the association of BB exposure was tested in PRP stratified groups in each of the 3 validation datasets using Cox models of survival (time to all-cause mortality). Our primary analysis consisted of models adjusted for MAGGIC (again without BB variable) (43) and BB propensity score, (44, 45) with BB exposure treated as a continuous variable. Given the relatively small sample sizes of the individual datasets, the results from each of the individual validation datasets were combined by meta-analysis using a fixed effect model to provide an overall validation of the PRP (n=l 188). We also tested for heterogeneity within the studies of the meta-analysis using Cohran's Q test and report this along with the I/\2 statistic. We then tested models inclusive of both PRP categories with an interaction term (PRP*BB) to calculate an interaction p value. We also present Kaplan-Maier curves in PRP stratified groups comparing baseline BB dose dichotomized into high vs. low exposure at a dose equivalent of <0.5 vs. ≥0.5, corresponding to half the target dose of BB in pivotal clinical trials (e.g. total daily dosage of 100 mg for metoprolol or 25 mg for carvedilol).

Since BB was not randomly assigned, we included propensity score adjustment for baseline BB use in all analyses. The propensity score was constructed using logistic regression predicting baseline BB using the following variables: Age, sex, creatinine, ischemic etiology, stroke, COPD, peripheral vascular disease, atrial fibrillation, and hypertension. The propensity scores were grouped into quartiles and this was used as a covariate (0, 1, 2, 3) in all analytic models. To verify the effectiveness of the propensity score for mitigating bias we performed a balance check by tabulating the weighted standardized difference for each covariate for each study. These ranged from 0.01 to 0.31 (Table 4), implying reasonably balanced covariates. (47)

Secondary analyses included similar models stratified by history of atrial fibrillation, and (separately) by EF category (<40% vs 40-49%) and examining cardiovascular (CV) death. Atrial fibrillation and EF categ01ies were examined in stratified Cox models with the same covariates as above. The time to CV death was analyzed using Fine-Gray models (to account competing risks) and including the same covariates as main survival analyses above. All BB exposures were constructed across agents using dose-equivalency as a proportion of the target dose of agent as previously described. (35) For HFPGR-test the BB exposure was time-updating measurements while for TIME-CHF and HF-ACTION the baseline BB dose was used.

Baseline characteristics are shown in total and across cohorts. Continuous variables were summarized by the mean and standard deviation and categorical variables were summarized by counts and percentages. They were compared among the datasets using analysis of variance (ANOVA) for continuous variables and Chi-square test for categorical variables. All statistical analyses were performed using R 3.6.1 (R Foundation, Vienna, Austria). P<0.05 was considered statistically significant.

Pharmacy Claims and Estimation of Beta-Blocker Exposure

To examine medication exposure of the BB class equivalent doses across agents were established. This was based on what proportion of a target dose for each specific agent was used, taken as the target dose for systolic HF used in clinical trials, or the maximum daily dose for BB agents that are not approved for use in treating systolic HF (e.g., atenolol). Specifically, these target/maximal daily doses were 50 mg for carvedilol, 200 mg for metoprolol (for both long-acting and short-acting formulations), lOmg for bisoprolol, 100 mg for atenolol, and 600 mg for labetalol. For example, 25 mg of carvedilol per day (i.e. 12.5 mg twice daily) was considered a 0.5 BB dose equivalent.

Chronic exposure to BB was then calculated as the drug-equivalent strength (described above) multiplied by the quantity of medication dispensed in a 6-month time block, divided by the total number of days in the 6-month time block. A specific BB exposure estimate was calculated for each patient for each day of follow up. Individual exposure measures reflected average exposure over the previous 6 months and could vary daily and could include periods of no exposure.

Results

Baseline characteristics of the 4 datasets (the 1 derivation and 3 validation, total n=1,436) are summarized in Table 2.

TABLE 2

Propensity Score Balance Check: Weighted Standardized Differences for each Cohort

| Variable | HFPGR-Derivation | HFPGR-Test | HF-ACTION | TDVIE-CHF |
|---|---|---|---|---|
| Age | 0.026 | 0.011 | 0.317 | 0.06 |
| Sex | 0.051 | 0.03 | 0.112 | 0.03 |
| COPD | 0.058 | 0.152 | 0.085 | 0.019 |
| Atrial Fibrillation | 0.04 | 0.109 | 0.067 | 0.008 |
| Ischemic Etiology | 0.008 | 0.087 | 0.217 | 0.13 |
| Stroke | 0.212 | 0.131 | 0.202 | 0.047 |
| Diabetes | 0.191 | 0.059 | 0.09 | 0.033 |
| Vascular Disease | 0.004 | 0.165 | 0.164 | 0.037 |
| Creatinine | 0.004 | 0.057 | 0.112 | 0.01 |
| Hypertension | 0.025 | 0.012 | NA | 0.185 |

The cohorts significantly differed in relation to all variables assessed, except for the frequency of diabetes and stroke. Notably the median BB dose/exposure varied, with HF-ACTION having a greater median (0.56 dose equivalents, representing half of target dose) compared to the other validation sets (0.28, 0.25 respectively for HFPGR and TIME-CHF). NTproBNP levels were greater in TIME-CHF and least in HF-ACTION. Average follow-up across datasets ranged from 785 to 985 days and there was a total of 332 deaths (23%).

The PRP was developed as described in the methods and it optimized after the inclusion of 44 genetic loci. The list of the 44 SNPs comprising the PRP (along with annotation) are provided in Table 3.

TABLE 3

List of 44 SNPs included in the BB polygenic response predictor (PRP).

| Location (GRCh37) | rsID | Imp. $r^2$ | Coeff. | MAF | p-value | Ref | Alt | Gene (SNP type) | Functional annotation in HaploReg# and GWAS catalog associations |
|---|---|---|---|---|---|---|---|---|---|
| 12:1053865 | rs4331189 | 0.95 | 4.36 | 0.14 | 2.63E−07 | T | c | C12orf45 | eQTL for C12orf45, SLC41A2, and MGC40397 |
| 12:10535324 | rs4075503 | 0.90 | 4.33 | 0.14 | 8.83E−07 | G | T | none | eQTL for SLC41A2 and C12orf45; possible reg. role to promoter histone mark, enhancer histone mark, Proteins bound & Motifs changed. |
| 5:2655779 | rs16870234 | 0.91 | 4.58 | 0.25 | 1.38E−06 | A | G | none | Possible regulatory role to enhancer histone marks and motifs changed. |
| 5:102978477 | rs75087282 | 0.86 | 4.71 | 0.12 | 1.52E−06 | A | G | none | possible regulatory role to 4 altered motifs |
| 12:1080482 | rs28548659 | 0.98 | 4.72 | 0.10 | 3.30E−06 | T | c | BTBD1 (intronic) | Possible regulatory role to 11 altered motifs |
| 4:11263913 | rs782760 | 0.88 | 3.60 | 0.28 | 4.14E−06 | c | A | none | Possible regulatory role to enhancer histone marks (ESDR and ESC) and motifs |
| 3:32526153 | rs367841 | 0.86 | 3.97 | 0.32 | 5.39E−06 | T | c | CMTM6 (intronic) | eQTL for CMTM6 and CMTM7; possible regulatory role to promoter histone marks (BLD), enhancer histone marks (ESDR, BLD), DNAse, Proteins bound and Motifs changed. |
| 20:50686015 | rs6013374 | 0.88 | 4.02 | 0.16 | 5.49E−06 | c | T | none | Possible regulatory role to Motifs changed (Evi-1) |
| 19:57887748 | rsl89508091 | 0.84 | 4.00 | 0.19 | 5.91E−06 | c | A | ZNF547 (intronic) | eQTL for ZNF304, CTC-444N24.13, ZNF749; possible regulatory role to DNAse (SKIN). |

TABLE 3-continued

List of 44 SNPs included in the BB polygenic response predictor (PRP).

| Location (GRCh37) | rsID | Imp. $r^2$ | Coeff. | MAF | p-value | Ref | Alt | Gene (SNP type) | Functional annotation in HaploReg[#] and GWAS catalog associations |
|---|---|---|---|---|---|---|---|---|---|
| 12:29688202 | rs299453 | 0.67 | 3.87 | 0.35 | 7.16E−06 | T | c | TMTC1 (intronic) | Possible reg. role to enhancer histone marks (LNG, FAT, BLD), DNAse (ESDR, MUS), proteins bound (CEBPB) and motifs changed (TATA, TBX5) |
| 12:29683110 | rs299445 | 0.66 | 3.86 | 0.35 | 7.65E−06 | c | T | TMTC1 (intronic) | Possible regulatory to enhancer histone mark (BLD) and motifs changed. |
| 12:10520008 | rs9737956 | 0.70 | 4.35 | 0.12 | 8.34E−06 | T | c | SLC41A2 (intronic) | Possible regulatory role to motifs changed (Irx) |
| 3:175421845 | rs6773175 | 0.85 | 4.07 | 0.16 | 8.50E−06 | A | G | NAALADL2 (intronic) | Possible reg role to enhancer histone marks (GI) & motifs changed (Nrf-2) |
| 3:10455742 | rs34912 | 0.87 | 3.39 | 0.32 | 1.01E−05 | T | A | ATP2B2 (intronic) | eQTL for GHRLOS; possible regulatory role to motifs changed (EBF, NF-KappaB, SZFl-1) |
| 18:68373609 | rs2457492 | 0.84 | 3.15 | 0.25 | 1.12E−05 | G | A | none | Possible regulatory role to enhancer histone mark (BLD) |
| 13:82134871 | rs2225686 | 0.97 | 3.22 | 0.47 | 1.14E−05 | T | G | none | Possible regulatory role to motifs changed (Myc, NF-kappaB, ZBTB33) |
| 12:29701516 | rs299468 | 0.71 | 3.80 | 0.35 | 1.14E−05 | c | T | TMTC1 (intronic) | Possible regulatory role to enhancer histone mark (MUS) & DNAse (BLD). |
| 17:48724199 | rs34221557 | 0.90 | 3.22 | 0.47 | 1.40E−05 | A | c | ABCC3 (intronic) | Possible regulatory role to enhancer histone marks |
| 5:102981016 | rs60529740 | 0.83 | 5.12 | 0.12 | 1.57E−05 | T | G | none | Possible regulatory role to enhancer histone marks |
| 9:14782367 | rs10810237 | 0.87 | 3.72 | 0.17 | 1.59E−05 | c | T | FREM1 (intronic) | Possible regulatory role to Motifs changed (HNF1, Ncx). |
| 9:14790092 | rs10756612 | 0.89 | 3.71 | 0.17 | 1.77E−05 | A | c | FREM1 (intronic) | Possible regulatory role to DNAse and motifs changed |
| 19:14839160 | rs4808387 | 0.86 | 3.99 | 0.28 | 1.88E−05 | c | T | ZNF333 (intronic) | eQTL for ZNF333, EMR2, DNAJBl and ADGRE2; possible regulatory role to motifs changed (lrf). |
| 8:26380683 | rs56098448 | 0.86 | 4.13 | 0.29 | 2.00E−05 | A | T | DPYSL2 (intronic) | Possible regulatory role to motifs changed. |
| 19:57688175 | rs34335569 | 0.88 | 3.82 | 0.19 | 2.11E−05 | A | G | none | eQTL for DUXA; possible regulatory role to motifs changed. |
| 2:172525144 | rs1399958* | NA | 4.14 | 0.12 | 2.12E−05 | T | c | none | eQTL for CYBRD1, HAT1, and AC068039.4; possible regulatory role to enhancer histone marks and motifs changed. |
| 8:133095617 | rs62521322 | 0.83 | 3.71 | 0.42 | 2.51E−05 | G | T | HHLA1 (intronic) | none |
| 10:22101608 | rs2666763 | 0.57 | 3.49 | 0.34 | 2.55E−05 | G | A | DNAJC1 (intronic) | possible regulatory role to motifs changed (E2F, TBX5, Zfx) |

TABLE 3-continued

List of 44 SNPs included in the BB polygenic response predictor (PRP).

| Location (GRCh37) | rsID | Imp. $r^2$ | Coeff. | MAF | p-value | Ref | Alt | Gene (SNP type) | Functional annotation in HaploReg# and GWAS catalog associations |
|---|---|---|---|---|---|---|---|---|---|
| 3:148661164 | rs4681163 | 0.81 | 3.31 | 0.23 | 2.68E−05 | G | A | none | eQTL for CPA3; possible regulatory role to enhancer histone marks and motifs changed. |
| 2:20669737 | rs12988451 | 0.96 | 3.58 | 0.44 | 2.70E−05 | A | G | none | eQTL for AC023137.2; possible regulatory role to enhancer histone marks, protein bounded (FOXA1), and motifs changed. |
| 4:166456085 | rs6828706 | 0.92 | 3.06 | 0.29 | 2.72E−05 | T | c | none | possible regulatory role to motifs changed (LUN-1). |
| 18:3056415 | rs60971978 | 0.78 | 3.79 | 0.30 | 2.98E−05 | T | G | none | Imporant regulatory role to enhancer histone marks and motifs changed. |
| 17:10829256 | rs4527059 | 0.96 | 3.89 | 0.21 | 3.19E−05 | A | G | none | Imporant regulatory role to DNAse and motifs changed. |
| 7:101285877 | rs2527834 | 0.99 | 3.60 | 0.44 | 3.32E−05 | T | c | none | possible regulatory role to motifs changed. |
| 6:109554233 | rs12528081 | 0.93 | 4.14 | 0.36 | 3.41E−05 | T | c | none | eQTL for CD164, RPI1-425D10.10 and CCDC162P; possible regulatory role to motifs changed (Smad). |
| 1:54772851 | rs4413992 | 0.74 | 3.26 | 0.40 | 3.48E−05 | A | G | SSBP3 (intronic) | Possible reg. role to enhancer histone marks & motifs changed (HEN1). |
| 11:1292172 | rs4514425 | 0.91 | 3.43 | 0.30 | 3.59E−05 | T | c | none | Possible regulatory role to DNAse and motifs changed. |
| 10:34802967 | rs4934638* | NA | 3.32 | 0.23 | 3.61E−05 | T | c | PARD3 (intronic) | Possible regulatory role to enhancer histone marks and motifs changed. |
| 19:2058694 | rs10416900 | 0.61 | 3.75 | 0.16 | 3.65E−05 | T | c | none | Possible regulatory role to DNAse and motifs changed. |
| 1:11606783 | rs61797384 | 0.86 | 5.15 | 0.13 | 3.90E−05 | c | T | none | eQTL for VANGL possible regulatory role to enhancer histone marks. DNAse, and motifs changed. |
| 3:44350264 | rs2171574 | 0.85 | 3.19 | 0.16 | 3.92E−05 | A | G | TOPA,Z1 (intronic) | eQTL for ZNF660, TCAIM, LINC00694, and RPI 1-424N24.2 |
| 3:10474448 | rs34854 | 0.79 | 3.27 | 0.22 | 3.97E−05 | T | c | ATP2B2 (intronic) | eQTL for GHRLOS and ATP2B2; possible regulatory role to enhancer histone marks, DNAse, |
| 17:7709088 | rs60764725 | 0.89 | 3.72 | 0.23 | 4.04E−05 | c | T | RBFOX3 (intronic) | eQTL for possible regulatory role to enhancer histone marks, DNAse and motifs changed. |
| 4:12052212 | rsl0518335 | 0.97 | 3.20 | 0.22 | 4.15E−05 | T | c | PDE5A (intronic) | eQTL for USP53, RPI 1-33B1.1, RP133B1.4, and possible reg. role to motifs changed. G/VAS association with acute myeloid leukemia |

TABLE 3-continued

List of 44 SNPs included in the BB polygenic response predictor (PRP).

| Location (GRCh37) | rsID | Imp. $r^2$ | Coeff. | MAF | p-value | Ref | Alt | Gene (SNP type) | Functional annotation in HaploReg# and GWAS catalog associations |
|---|---|---|---|---|---|---|---|---|---|
| 10:2188918 | rs6577189 | 0.86 | 3.25 | 0.35 | 4.29E−05 | A | G | MLLTI (intronic) | eQTL for MLLTIO; possible regulatory role to enhancer histone marks & motifs changed. GWAS association to urinary albumin to creatinine ratio. |

*SNP genotyped on array (all others were imputed).

P values shown are for the SNP*BB interaction term in the derivation cohort (HFPGR-derivation) with genomic control.

Imp. = Imputation

The interaction effect between each of them and BB exposure was associated with mortality (p<10-4). The percentile of PRP that resulted in the best separation between BB responders and non-responders in the HFPGR derivation dataset was the 30th percentile (raw score=68.14) and this was used as the dichotomization point for validation testing. In HF-ACTION, 3 of the 44 SNI>s of the PRP did not have usable genotype calls so the remaining 41 SNPs were used to tabulate the PRP for HF-ACTION participants and the 30th percentile (based on this 41-SNP score) was re-tabulated in the derivation set and used as the dichotomization point for HF-ACTION validation testing. Based on the results from the derivation dataset, patients with a low PRP were hypothesized to be the BB responders in the validation datasets, and patients with a high PRP were hypothesized to be BB non-responders.

Figure 3:
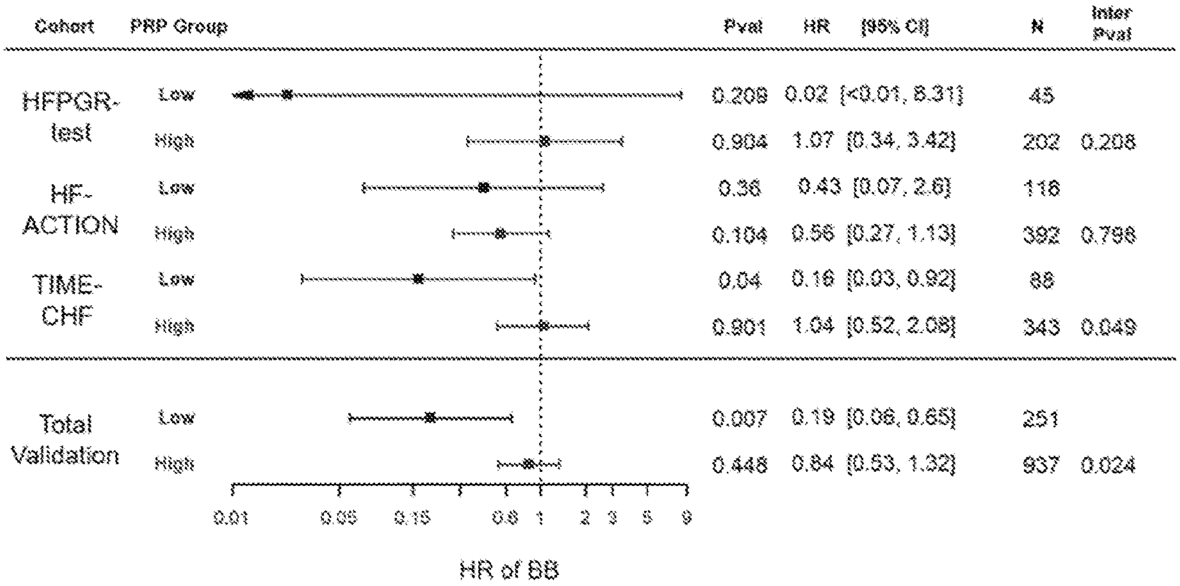
FIG. 3. depicts a forest plot of hazard ratios for BB exposure in each of the validation cohorts and for the total validation (meta-analysis). The optimal PRP score cutoff from the derivation dataset was tested in Cox proportional hazards models adjusted for MAGGIC (43) and BB propensity score (44, 45). Low and high PRP indicate values above or below threshold (30th percentile of the derivation set). BB=Beta-blocker; PRP=polygenic response predictor FIGS. 4A, 4B, and 4C. depicts Kaplan Meier survival curves stratified by PRP (high vs. low) and BB exposure for each dataset. The left panels show patients with a low PRP and the right-sided panels show patients with a high PRP. The red curves are patients with high BB exposure (2:50% target dose), and blue curves are patients with low BB exposure. BB=Beta-blocker; PRP=polygenic response predictor.
Figure 4A:
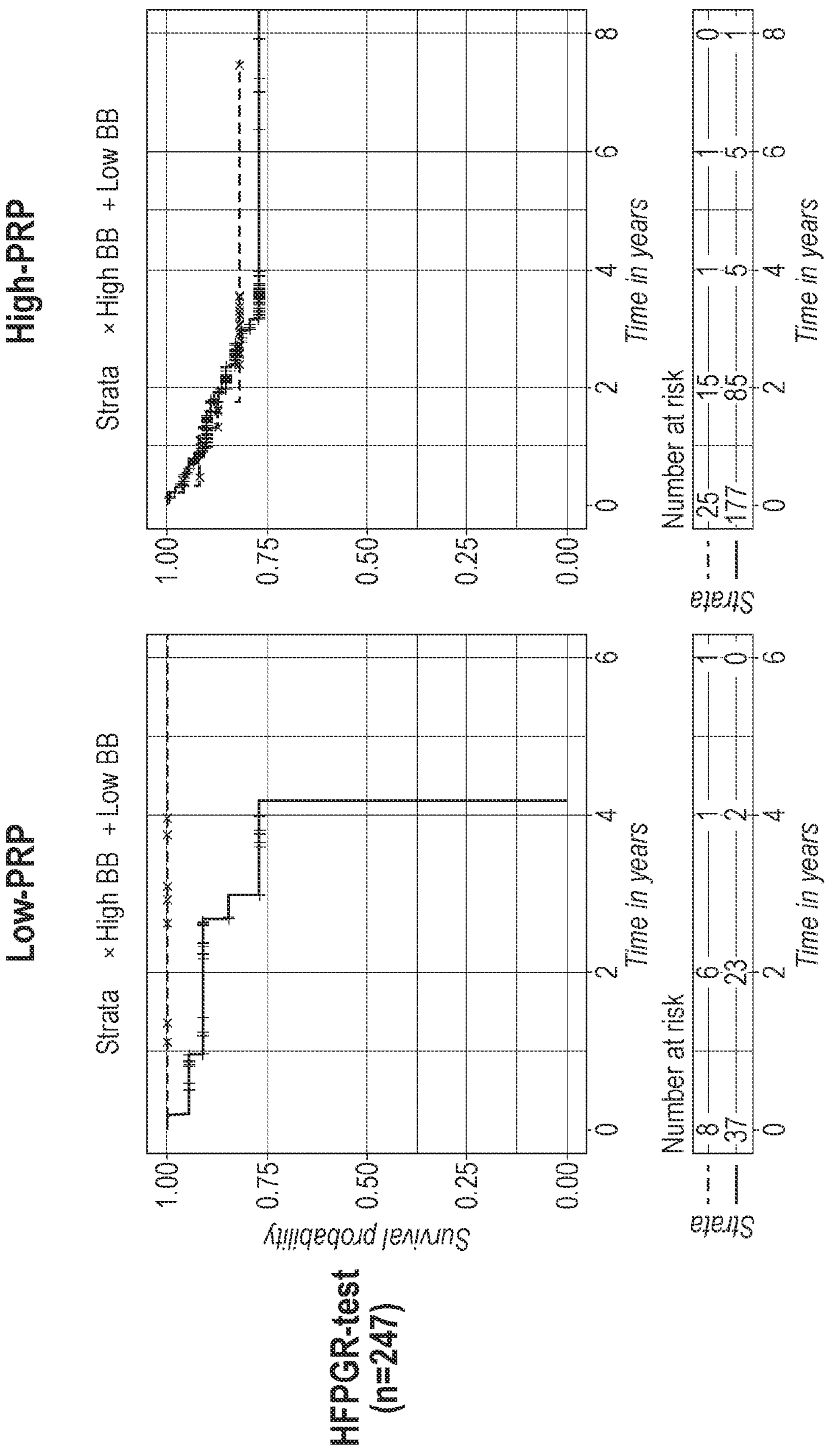
Figure 4B:
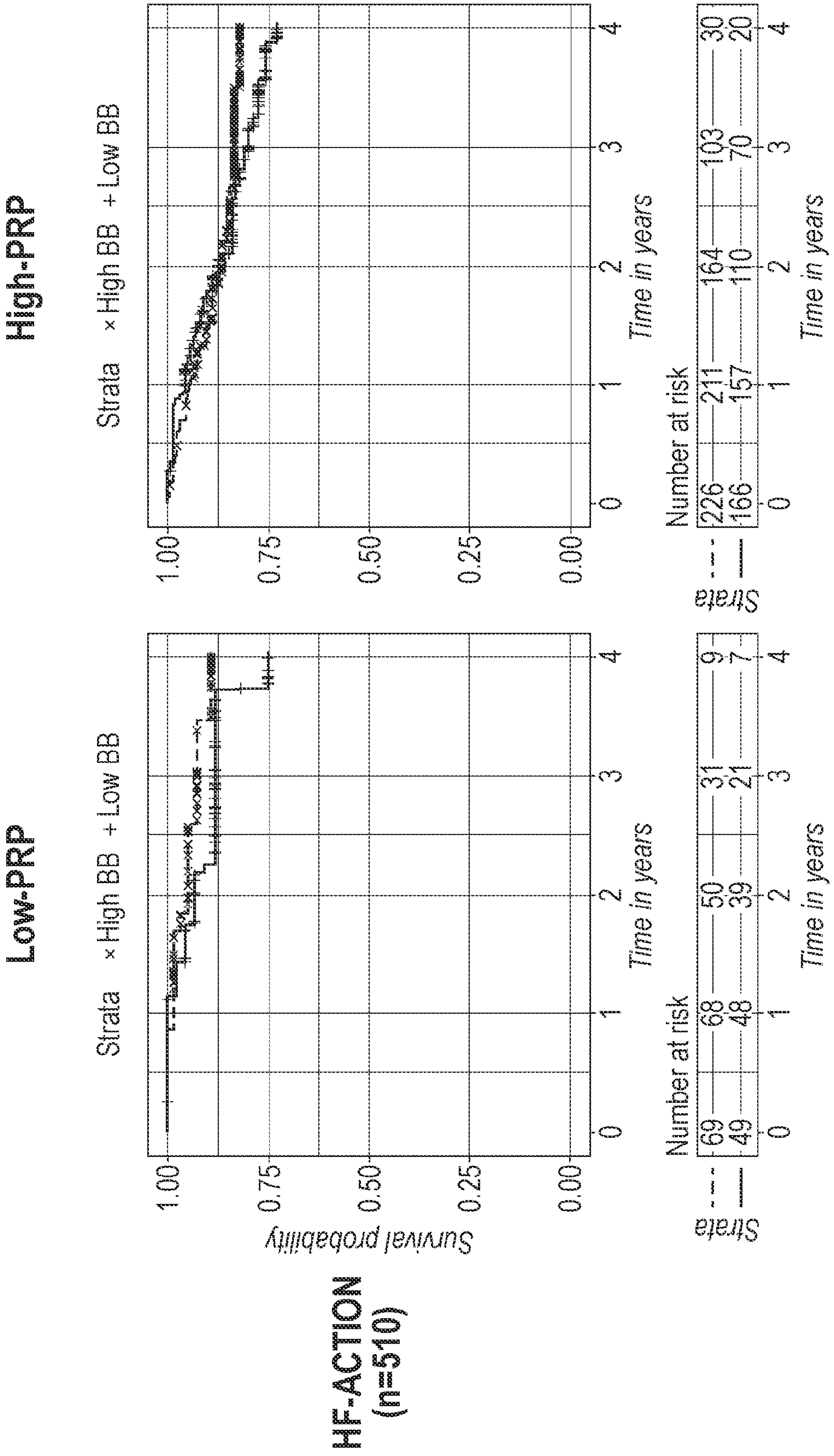
Figure 4C:
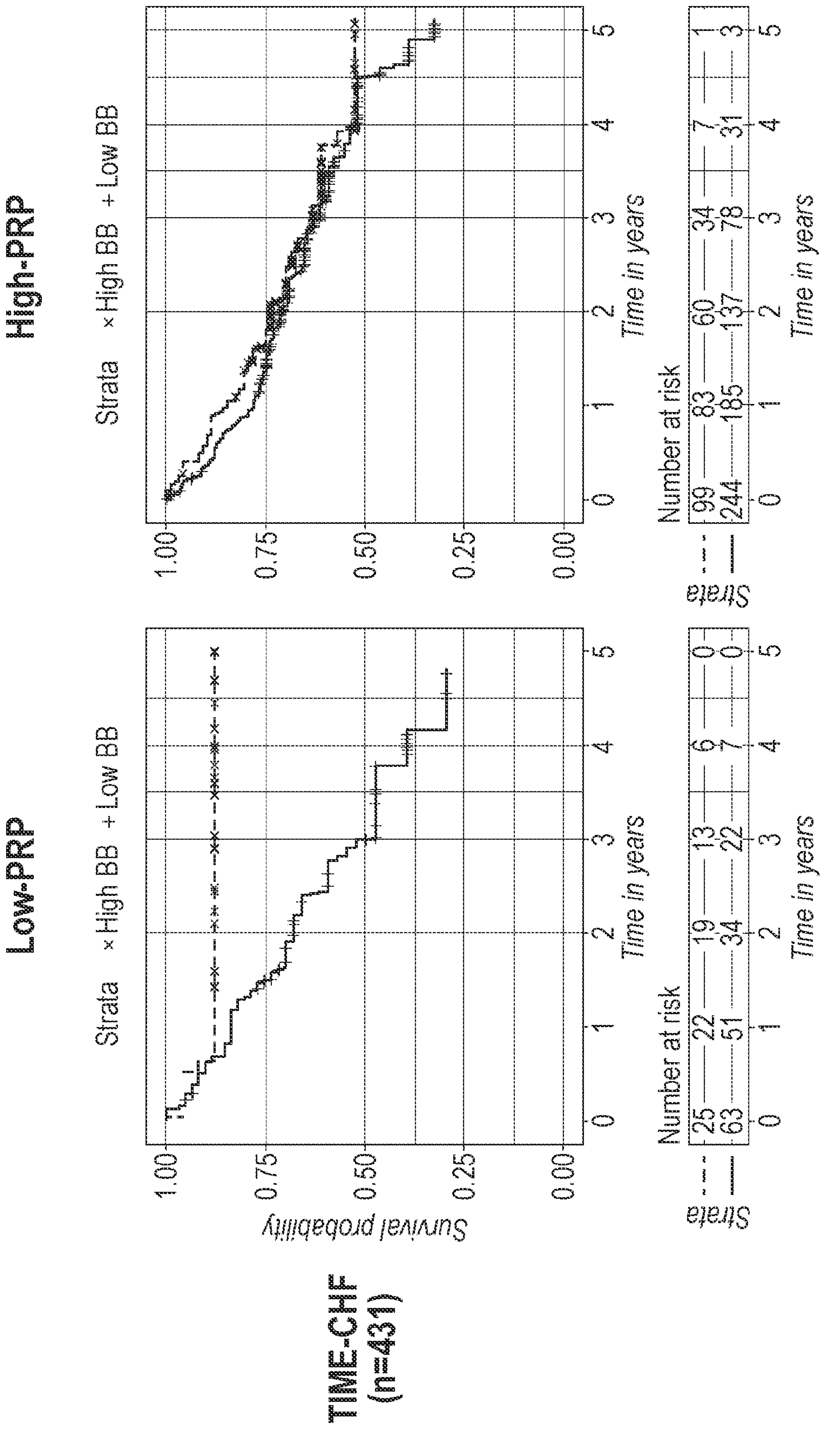

The hazard ratios for BB exposure (as a continuous variable incorporating dose) in each of the validation datasets and in the overall validation group (combined via fixed-effect meta-analysis) are displayed in FIG. 3. The corresponding survival curves (with BB exposure dichotomized at 50% target dose using the baseline dosing) are shown in FIGS. 4A, 4B and 4C. The hazard ratio for BB exposure was numerically lower (more protective) in all the low-PRP groups than in the corresponding high-PRP groups, however, the confidence intervals were wide within the individual datasets, reaching significance in TilvlE-CHF. The entire validation group testing included 1,188 patients overall and a total of 279 deaths (23.5% mortality). This analysis revealed a very strong and statistically significant protective association for BB in the low-PRP group (HR=0.19 [95% CI=0.058-0.64] p=0.0075), but no significant association in the high-PRP group (HR=0.84 [95% CI 0.53-1.3] p=0.45). Formal test of interaction indicated a significant difference between the BB effect between PRP groups (interaction p=0.0235). Of note, PRP group (high vs. low) was not itself significantly associated with mortality (HR=0.83, p=0.37), and there was no difference in heartrate by PRP category within any of the cohorts (all p>0.05). Tests for heterogeneity in the meta-analysis resulted in a Cochran Q of 2.18 (p=0.34) and Y'2 statistic of 0.08, suggesting no significant heterogeneity.

Further experiments were conducted to evaluate a series of additional sensitivity analyses. Since atrial fibrillation has been associated with impaired BB effectiveness in pooled subgroup analyses of BB pivotal trials, we performed additional modeling stratified by baseline history atrial fibrillation in the validation dataset. Overall, there were 364 patients with history of atrial fibrillation and 824 without. Among those without atrial fibrillation the low-PRP group showed a BB HR of 0.33 (p=0.11) while the corresponding high-PRP group BB HR was 0.73 (p=0.31). In HFrEF patients with comorbid atrial fibrillation, those with a low-PRP had a BB HR of 0.063 (p=0.017) while the comparable high-PRP group showed a BB HR of 0.96 (p=0.92). Similarly, since we included patients with EF<50% in our study but HFrEF has more recently been defined as EF<40%, we also performed secondary analyses stratified by EF category (<40% vs 40-49%). Overall, there were 971 patients with EF<40% and 217 with EF 40-49%, and in both subgroups the PRP trended towards predicting BB response with HR similar to the total validation analysis. In those with EF<40% and low-PRP the BB-HR was 0.23 (p=0.0203) while in the high-PRP patients BB-HR was 0.87 (p=0.57). In patients with baseline EF 40-49% and low-PRP the BB-HR was 0.053 (p=0.23) while in the corresponding high-PRP patients the BB-HR was 0.82 (p=0.76). Finally, we also tested PRP performance in terms of BB exposure association to cardiovascular (CV) death. There were a total of 200 CV death events modeled across the validation cohorts using a Fine-Gray model (to account competing risks) and the same covariates as above. The results are summarized in Table 4. In the total validation meta-analysis the HR of BB in low-PRP was 0.19 (95% CI 0.044-0.804) and HR of BB in the high-PRP was 0.89 (95% CI 0.51-1.5), and a test of interaction that was statistically significant (p=0.046).

Discussion

Neither previous candidate gene studies nor clinical predictors have been able to better target BB therapy from the broad indication achieved in HFrEF clinical trials. The PRP, a weighted calculation of genotypes at 44 loci across the genome, was able to do this in a validation group of more than 1100 patients. While polygenic scores specific for drug-response have been described, (10, 25-34) ours is the first validated example that we are aware of relevant to HF treatment, and one of the first in cardiovascular disease. The results provided herewith are provocative, but the potential implications are wide ranging.

The approach and findings of the present disclosure advance the existing literature on polygenic scores, which have been described for disease risk in variety of settings, (48, 49) including some cardiovascular diseases such as coronary artery disease (49) and atrial fibrillation. (50) Some investigators have taken these scores (for disease-risk) and then layered on drug therapy, (25) while we have tried to go a step further by focusing on drug response (i.e. gene*drug interaction). This interaction approach has received less attention and presents unique challenges, such more complex statistical modeling and inherently lower power. The distinction is important however, because disease-risk (like pretest probability) is only one factor impacting treatment effectiveness, and existing evidence suggests distinct genetic architecture for drug response vs. disease-risk. (34, 51) Approaches somewhat similar to ours have been described with varying levels of success in other disease areas, (10, 25-34) to which our data bring some additional optimism. Our sample size is not dissimilar from many early drug development programs, and the idea that greater definition of the "responder" subset could routinely be had for many medications is obviously very alluring. This approach could amplify effect sizes (shrinking sample size requirements in pivotal trials), and ultimately reduce health care costs and adverse events by avoiding treatment in patients unlikely to be benefitted.

An inspection of the exemplified results raises a few observations that are worthy of note. One is that our BB PRP appeared of modest effect in HF-ACTION while the effect estimates in the other two validation cohorts were more dramatic, with the PRP being most statistically significant in TIME-CHF. The individual validation sets each had small sample sizes, so substantial variability across them is expected. Differences in the studies may also play a role. Specifically, HFPGR and TIME-CHF had more patients not treated with BB at baseline, and a lower average BB exposure, compared to HF-ACTION. In HF-ACTION, roughly 95% of patients in the parent study were treated with BB (37) and indeed 94% of patients in the ACTION-HF subcohort of the current study. This reflects care more consistent with current guidelines, but the reduced variability in BB exposure (i.e. near uniform use) reduces power to detect gene-drug interactions which is impacted by how many patients are unexposed to treatment. On the other hand, the patients in the TIME-CHF were the highest risk of the 3 studies and it included the highest number and proportion of deaths, providing relatively greater power to detect a differences in BB-associated survival compared to the other two datasets.

Despite all this, since each of the individual datasets is likely underpowered the more important consideration is that the overall validation result was quite clear and the direction of the association was consistent across all 3 datasets. Another point of potential interest is that the cut-off for favorable BB-response optimized at roughly 30% of the population. This suggests that most of the benefit of BB occurs in roughly one third of the population while the majority of patients show little, if any, benefit. This may seem counter-intuitive for a therapy with population average benefit, but mathematically a smaller 'super-responder' group is a plausible explanation for an overall benefit, and proportion is consistent with some data showing that a marked and sustained EF response to BB occurs in only a minority of patients. (52) The prospect of identifying a smaller, hyper-responsive subgroup for BB (or eventually other HF treatments) via polygenic scores is tempting to speculate about since this could allow individualized drug therapy and reduce the typical polypharmacy of HF; many patients do not tolerate target doses of all indicated agents (53) and these data highlight a potential solution to this real-world difficulty.

Since the PRP was derived by unbiased methodology (not based on pre-existing molecular biological knowledge) it may not be surprising that the loci of interest do not reflect established BB associations; a phenomenon previous seen in pharmacogenomic GWAS. (10, 54) Given the number of loci that inform the PRP and the fact that some are of unknown genomic function, a full interrogation of the mechanisms potentially at play remains a future endeavor, however, some pathways that indicate potential biologic plausibility are worth briefly noting. For instance, the top PRP loci is in ABCC3 a transporter that is associated with multidrug resistance, has been shown to alter propranolol cellular efflux, (55) and could theoretically impact BB absorption or transport. The second gene of interest, ATP2B2a, generated two loci of the PRP and is a plasma membrane $ca+^2$ transporter. While a specific mechanism is not established, it is well known that Ca homeostasis is critical in heart failure (56, 57) and is impacted by BB therapy. (58) Finally, variation in PDE5A was also a contributor to PRP and this gene's product has well known cardiovascular effects though specifics to BB response in HF are unknown.

The BB PRP score was only derived and validated in HFrEF patients of European ancestry. Thus, this BB PRP does not apply to patients of other ancestries. While we have previously shown that overall BB response appears similar by race and by genomic ancestry, (35) the individual genetic loci that determine this are likely to be very different across these groups due to different linkage patterns or even differing biologic drivers of response. A critical future undertaking is the construction of BB PRP score for other ancestral groups (e.g. African or Asian ancestry), or ideally, a score robust to ancestry. The present studies attempted to minimize the treatment bias and other potential confounders by adjusting all models for baseline clinical risk (via MAGGIC risk score) and as well as BB propensity score. (44, 45) Lastly, the strategy of keeping the completely distinct validation group relatively larger and including all 3 parent studies therein was preferred in order to maintain adequate validation sample size to test for survival differences and maximize the rigor and generalizability of our findings.

In summary, the present example has demonstrated the synthesis and validation of the first PRP score for BB survival benefit in heart failure patients of European ancestry. The PRP score was able to differentiate patients with a greatly enhanced BB-associated survival benefit from a larger group of patients that did not feature a statistically significant survival benefit. These findings challenge the "one size fits all" approach for BB treatment in heart failure (6) and are a step toward precision medicine for heart failure. The results of this PRP score analysis can be further refined and supplemented by analyzing additional genome-wide association study (GWAS) data, which are publicly available or are generated in future GWAS studies.

REFERENCES

1. Investigators M-H. Effect of metoprolol cr/xl in chronic heart failure: Metoprolol cr/xl randomised intervention trial in congestive heart failure (merit-hf). *Lancet.* 1999; 353:2001-2007

2. The cardiac insufficiency bisoprolol study ii (cibis-ii): A randomised trial. *Lancet.*
1999; 353:9-13

3. Packer M, Fowler M B, Roecker E B, Coats A J, Katus H A, Krum H, Mohacsi P, Rouleau J L, Tendera M, Staiger C, Holcslaw T L, Amann-Zalan I, DeMets D L, Carvedilol Prospective Randomized Cumulative Survival Study G. Effect of carvedilol on the morbidity of patients with severe chronic heart failure: Results of the carvedilol prospective randomized cumulative survival (copemicus) study. *Circulation.*
2002; 106:2194-2199
4. Metra M, Giubbini R, Nodari S, Baldi E, Modena M G, Dei Cas L. Differential effects of beta-blockers in patients with heart failure: A prospective, randomized, double-blind comparison of the long-term effects of metoprolol versus carvedilol. *Circulation.*
2000; 102:546-551
5. Roden D M, George A L, Jr. The genetic basis of variability in drug responses. *Nat Rev Drug Discov.* 2002; 1:37-44
6. Yancy C W, Jessup M, Bozkurt B, Butler J, Casey D E, Jr., Colvin M M, Drazner M H, Filippatos G S, Fonarow G C, Givertz MJVI, Hollenberg S M, Lindenfeld J, Masoudi F A, McBride P E, Peterson P N, Stevenson L W, Westlake C. 2017 acc/aha/hfsa focused update of the 2013 accf/aha guideline for the management of heart failure: A report of the american college of cardiology/american heart association task force on clinical practice guidelines and the heart failure society of America. *Circulation.* 2017; 136:el37-el61
7. Rienstra M, Damman K, Mulder B A, Van Gelder I C, McMurray J J, Van Veldhuisen D J. Beta-blockers and outcome in heart failure and atrial fibrillation: A meta-analysis. *JACC. Heart failure.* 2013; 1:21-28
8. Kotecha D, Holmes J, Krum H, Altman D G, Manzano L, Cleland J G, Lip G Y, Coats A J, Andersson B, Kirchhof P, van Lueder T G, Wedel H, Rosano G, Shibata M C, Rigby A, Flather M D, Beta-Blockers in Heart Failure Collaborative G. Efficacy of beta blockers in patients with heart failure plus atrial fibrillation: An individual-patient data meta-analysis. *Lancet.* 2014; 384:2235-2243
9. Talameh J A, Lanfear D E. Pharmacogenetics in chronic heart failure: New developments and current challenges. *Current heart failure reports.* 2012; 9 23-32
10. Shahin M H, Conrado D J, Gonzalez D, Gong Y, Lohmeyer M T, Beitelshees A L, Boerwinkle E, Gums J G, Chapman A, Turner S T, Cooper-DeHoff RJ\11, Johnson J A. Genome-wide association approach identified novel genetic predictors of heart rate response to beta-blockers. *J Am Heart Assoc.* 2018; 7
11. Parikh K S, Fiuzat M, Davis G, Neely M, Blain-Nelson P, Whellan D J, Abraham W T, Adams K F, Jr., Felker G M, Liggett S B, O'Connor C M, Bristow M R. Dose response of beta-blockers in adrenergic receptor polymorphism genotypes. *Circ Genom Precis Med.* 2018; ll:e002210
12. Johnson J A, Liggett S B. Cardiovascular pharmacogenomics of adrenergic receptor signaling: Clinical implications and future directions. *Clin Pharmacol Ther.* 2011; 89:366-378
13. Shin J, Johnson J A. Pharmacogenetics of beta-blockers. *Pharmacotherapy.* 2007; 27:874-887
14. Fiuzat M, Neely M L, Starr A Z, Kraus W E, Felker G M, Donahue M, Adams K, Pina I L, Whellan D, O'Connor C M. Association between adrenergic receptor genotypes and beta-blocker dose in heart failure patients: Analysis from the hf-action DNA substudy. *Eur J Heart Fail.* 2013; 15:258-266
15. Cresci S, Dorn G W, 2nd, Jones P G, Beitelshees A L, Li A Y, Lenzini P A, Province M A, Spertus J A, Lanfear D E. Adrenergic-pathway gene variants influence beta-blocker-related outcomes after acute coronary syndrome in a race-specific manner. *J Am Coll Cardiol.* 2012; 60:898-907
16. Luzum J A, English J D, Ahmad U S, Sun J W, Canan B D, Sadee W, Kitzmiller J P, Binkley P F. Association of genetic polymorphisms in the beta-I adrenergic receptor with recovery of left ventricular ejection fraction in patients with heart failure. *J Cardiovasc Transl Res.* 2019; 12:280-289
17. Yancy C W, Jessup M, Bozkurt B, Butler J, Casey D E, Jr., Drazner M H, Fonarow G C, Geraci S A, Horwich T, Januzzi J L, Johnson M R, Kasper E K, Levy W C, Masoudi F A, McBride P E, McMurray J J, Mitchell J E, Peterson P N, Riegel B, Sam F, Stevenson L W, Tang W H, Tsai E J, Wilkoff B L. 2013 accf/aha guideline for the management of heart failure: A report of the american college of cardiology foundation/american heart association task force on practice guidelines. *J Am Coll Cardiol.* 2013; 62:el47-239
18. Claassens D M F, Vos G J A, Bergmeijer T O, Hermanides R S, van't Hof A W J, van der Harst P, Barbato E, Morisco C, Tjon Joe Gin R M, Asselbergs F W, Mosterd A, Herrman J R, Dewilde W J M, Janssen P W A, Kelder J C, Postma M J, de Boer A, Boersma C, Deneer V H M, Ten Berg J M. A genotype-guided strategy for oral p2y l2 inhibitors in primary pci.
*The New England journal of medicine.* 2019
19. Bodmer W, Bonilla C Common and rare variants in multifactorial susceptibility to common diseases. *Nature genetics.* 2008; 40:695-701
20. Gibson G. On the utilization of polygenic risk scores for therapeutic targeting. *PLoS genetics.* 2019; 15:el008060
21. Tansey K E, Guipponi M, Hu X, Domenici E, Lewis G, Malafosse A, Wendland J R, Lewis C M, McGuffin P, Uher R. Contribution of common genetic variants to antidepressant response. *Biological psychiatry.* 2013; 73:679-682
22. Che R, Motsinger-Reif A A Evaluation of genetic risk score models in the presence of interaction and linkage disequilibrium. *Frontiers in genetics.* 2013; 4: 138
23. Kathiresan S, Melander 0, Anevski D, Guiducci C, Burtt N P, Roos C, Hirschhorn J N, Berglund G, Hedblad B, Groop L, Altshuler D M, Newton-Cheh C, Orho-Melander M. Polymorphisms associated with cholesterol and risk of cardiovascular events. *The New England journal of medicine.* 2008; 358: 1240-1249
24. Kathiresan S, Willer C J, Peloso G M, Demissie S, Musunuru K, Schadt E E, Kaplan L, Bennett D, Li Y, Tanaka T, Voight B F, Bonnycastle L L, Jackson A U, Crawford G, Surti A, Guiducci C, Burtt N P, Parish S, Clarke R, Zelenika D, Kubalanza K A, Morken M A, Scott L J, Stringham H M, Galan P, Swift A J, Kuusisto J, Bergman R N, Sundvall J, Laakso M, Ferrucci L, Scheet P, Sanna S, Uda M, Yang Q, Lunetta K L, Dupuis J, de Bakker P I, O'Donnell C J, Chambers J C, Kooner J S, Hercberg S, Meneton P, Lakatta E G, Scuteri A, Schlessinger D, Tuomilehto J, Collins F S, Groop L, Altshuler D, Collins R, Lathrop G M, Melander 0, Salomaa V, Peltonen L, Orho-Melander M, Ordovas J M, Boehnke M, Abecasis G R, Mohlke K L, Cupples L A. Common variants at 30 loci contribute to polygenic dyslipidemia. *Nat Genet.* 2009; 41:56-65
25. Natarajan P, Young R, Stitziel N O, Padmanabhan S, Baber U, Mehran R, Sartori S, Fuster V, Reilly D F, Butterworth A, Rader D J, Ford I, Sattar N, Kathiresan S. Polygenic risk score identifies subgroup with higher burden of atherosclerosis and greater relative
benefit from statin therapy in the primary prevention setting. *Circulation.* 2017; 135:2091-2101

26. Shahin M H, Gong Y, McDonough C W, Rotroff D M, Beitelshees A L, Garrett T J, Gums J G, Motsinger-Reif A, Chapman A B, Turner S T, Boenvinkle E, Frye R F, Fiehn O, Cooper-DeHoff R M, Kaddurah-Daouk R, Johnson J A. A genetic response score for hydrochlorothiazide use: Insights from genomics and metabolomics integration. *Hypertension.* 2016; 68:621-629

27. Gong Y, McDonough C W, Wang Z, Hou W, Cooper-DeHoff Rlvf, Langaee T Y, Beitelshees A L, Chapman A B, Gums J G, Bailey K R, Boerwinkle E, Turner S T, Johnson J A. Hypertension susceptibility loci and blood pressure response to antihypertensives: Results from the pharmacogenomic evaluation of antihypertensive responses study. *Circulation. Cardiovascular genetics.* 2012; 5:686-691

28. Hettige N C, Cole C B, Khalid S, De Luca V. Polygenic risk score prediction of antipsychotic dosage in schizophrenia. *Schizophrenia research.* 2016; 170:265-270

29. Alemany-Navarro M, Costas J, Real E, Segalas C, Bertolin S, Domenech L, Rabionet R, Carracedo A, Menchon J M, Alonso P. Do polygenic risk and stressful life events predict pharmacological treatment response in obsessive compulsive disorder? A gene-environment interaction approach. *Translational psychiatry.* 2019; 9:70

30. Mega J L, Stitziel N O, Smith J G, Chasman D I, Caulfield M, Devlin J J, Nordio F, Hyde C, Cannon C P, Sacks F, Poulter N, Sever P, Ridker P M, Braunwald E, Melander 0, Kathiresan S, Sabatine M S. Genetic risk, coronary heart disease events, and the clinical benefit of statin therapy: An analysis of primary and secondary prevention trials. *Lancet.* 2015; 385:2264-2271

31. Strauss D G, Vicente J, Johannesen L, Blinova K, Mason J W, Weeke P, Behr E R, Roden D M, \\lToosley R, Kosova G, Rosenberg M A, Newton-Cheh C. Common genetic variant risk score is associated with drug-induced qt prolongation and torsade de pointes risk: A pilot study. *Circulation.* 2017; 135:1300-1310

32. Lewis J P, Backman J D, Reny J L, Bergmeijer T O, Mitchell B D, Ritchie M D, Dery J P, Pakyz R E, Gong L, Ryan K, Kim E Y, Aradi D, Fernandez-Cadenas I, Lee M T M, Whaley R M, Montaner J, Gensini G F, Cleator J H, Chang K, Holmvang L, Hochholzer W, Roden D M, Winter S, Altman R, Alexopoulos D, Kim H S, Gawaz M, Bliden K, Valgimigli M, Marcucci R, Campo G, Schaeffeler E, Dridi N P, Wen M S, Shin J G, Fontana P, Giusti B, Geisler T, Kubo M, Trenk D, Siller-Matula Thf, Ten Berg J M, Gurbel P A, Schwab M, Klein T E, Shuldiner i\R. Pharmacogenomic polygenic response score predicts ischemic events and cardiovascular mortality in clopidogrel-treated patients. *European heart journal. Cardiovascular pharmacotherapy.* 2019

33. Wimberley T, Gasse C, Meier S M, Agerbo E, Maccabe J H, Horsdal H T. Polygenic risk score for schizophrenia and treatment-resistant schizophrenia. *Schizophrenia bulletin.* 2017; 43: 1064-1069

34. Garcia-Gonzalez J, Tansey K E, Hauser J, Henigsberg N, Maier W, Mors 0, Placentino A, Rietschel M, Souery D, Zagar T, Czerski P M, Jerman B, Buttenschon H N, Schulze T G, Zobel A, Farmer A, Aitchison K J, Craig I, McGuffin P, Giupponi M, Perroud N, Bondolfi G, Evans D, O'Donovan M, Peters T J, Wendland J R, Lewis G, Kapur S, Perlis R, Arolt V, Domschke K, Breen G, Curtis C, Sang-Hyuk L, Kan C, Newhouse S, Patel H, Baune B T, Uher R, Lewis C M, Fabbri C. Pharmacogenetics of antidepressant response: A polygenic approach. *Progress in neuro-psychopharmacology & biological psychiatry.* 2017; 75: 128-134

35. Luzum J A, Peterson E, Li J, She R, Gui H, Liu B, Spertus J A, Pinto Y M, Williams L K, Sabbah H N, Lanfear D E. Race and beta-blocker survival benefit in patients with heart failure: An investigation of self-reported race and proportion of african genetic ancestry. *J Am Heart Assoc.* 2018; 7

36. Pfisterer M, Buser P, Rickli H, Gutmann M, Erne P, Rickenbacher P, Vuillomenet A, Jeker U, Dubach P, Beer H, Yoon S I, Suter T, Osterhues H H, Schieber M}vf, Hilti P, Schindler R, Brunner-La Rocca H P, Investigators T-C. Bnp-guided vs symptom-guided heart failure therapy: The trial of intensified vs standard medical therapy in elderly patients with congestive heart failure (time-chi) randomized trial. *JAMA.* 2009; 301:383-392

37. O'Connor C M, Whellan D J, Lee K L, Keteyian S J, Cooper L S, Ellis S J, Leifer E S, Kraus W E, Kitzman D W, Blumenthal J A, Rendall D S, Miller N H, Fleg J L, Schulman K A, McKelvie R S, Zannad F, Pina I L, Investigators H-A. Efficacy and safety of exercise training in patients with chronic heart failure: Hf-action randomized controlled trial. *JAMA: the journal of the American Medical Association.* 2009; 301: 1439-1450

38. Lanfear D E, Hrobowski T N, Peterson E L, Wells K E, Swadia T V, Spertus J A, Williams L K. Association of beta-blocker exposure with outcomes in heart failure differs between african american and white patients. *Circ Heart Fail.* 2012; 5:202-208

39. McKee P A, Castelli W P, McNamara P M, Kannel W B. The natural history of congestive heart failure: The framingham study. *The New England journal of medicine.* 1971; 285:1441-1446

40. l\liller S A, Dykes D D, Polesky H F. A simple salting out procedure for extracting DNA from human nucleated cells. *Nucleic acids research.* 1988; 16:1215

41. Das S, Forer L, Schonherr S, Sidore C, Locke A E, Kwong A, Vrieze S I, Chew E Y, Levy S, McGue M, Schlessinger D, Stambolian D, Loh P R, Iacono W G, Swaroop A, Scott L J, Cucca F, Kronenberg F, Boehnke M, Abecasis G R, Fuchsberger C. Next-generation genotype imputation service and methods. *Nature genetics.* 2016; 48: 1284-1287

42. Genomes Project C, Auton A, Brooks L D, Durbin R M, Garrison E P, Kang H M, Korbel J O, Marchini J L, McCarthy S, McVean G A, Abecasis G R. A global reference for human genetic variation. *Nature.* 2015; 526:68-74

43. Pocock S J, Ariti C A, McMurray J J, Maggioni A, Kober L, Squire I B, Swedberg K, Dobson J, Poppe K K, Whalley G A, Doughty R N, Meta-Analysis Global Group in Chronic Heart F. Predicting survival in heart failure: A risk score based on 39 372 patients from 30 studies. *European heart journal.* 2013; 34:1404-1413

44. Rosenbaum P R, Rubin D B. The central role of the propensity score in observational studies for causal effects. *Biometrika.* 1983; 70:41-55

45. D'Agostino R B, Jr. Propensity score methods for bias reduction in the comparison of a treatment to a non-randomized control group. *Statistics in medicine.* 1998; 17:2265-2281

46. Simon R M, Subramanian J, Li M C, Menezes S. Using cross-validation to evaluate predictive accuracy of survival risk classifiers based on high-dimensional data. *Briefings in bioiriformatics.* 2011; 12:203-214

47. Cohen J. *Statistical power analysis for the behavioral sciences*. New York: Academic Press; 1977.

48. Torkamani A, Wineinger N E, Topol E J. The personal and clinical utility of polygenic risk scores. *Nature reviews. Genetics.* 2018; 19:581-590

49. Khera A V, Chaffin M, Aragam K G, Haas M E, Roselli C, Choi S H, Natarajan P, Lander E S, Lubitz S A, Ellinor P T, Kathiresan S. Genome-wide polygenic scores for common diseases identify individuals with risk equivalent to monogenic mutations. *Nat Genet.* 2018; 50: 1219-1224

50. Weng L C, Preis S R, Hulme O L, Larson M G, Choi S H, Wang B, Trinquart L, McManus D D, Staerk L, Lin H, Lunetta K L, Ellinor P T, Benjamin E J, Lubitz S A. Genetic predisposition, clinical risk factor burden, and lifetime risk of atrial fibrillation. *Circulation.* 2018; 137: 1027-1038

51. Dorling L, Kar S, Michailidou K, Hiller L, Vallier A L, Ingle S, Hardy R, Bowden S J, Dunn J A, Twelves C, Poole C J, Caldas C, Earl H M, Pharoah P D, Abraham J E. The relationship between common genetic markers of breast cancer risk and chemotherapy-induced toxicity: A case-control study. *PloS one.* 2016; 11:e0158984

52. Metra M, Nodari S, Parrinello G, Giubbini R, Manca C, Dei Cas L. Marked improvement in left ventricular ejection fraction during long-term beta-blockade in patients with chronic heart failure: Clinical correlates and prognostic significance. *American Heart Journal.* 2003; 145: 292-299

53. Ghanem C I, Manautou J E. Modulation of hepatic mrp3/abcc3 by xenobiotics and pathophysiological conditions: Role in drug pharmacokinetics. *Curr Med Chem.* 2019; 26: 1185-1223

54. McDonough C W, Gong Y, Padmanabhan S, Burkley B, Langaee T Y, Melander O, Pepine C J, Dominiczak A F, Cooper-Dehoff R M, Johnson J A. Pharmacogenomic association of nonsynonymous snps in siglecl2, albg, and the selectin region and cardiovascular outcomes. *Hypertension.* 2013; 62:48-54

55. Jarvinen E, Troberg J, Kidron H, Finel M. Selectivity in the efflux of glucuronides by human transporters: Mrp4 is highly active toward 4-methylumbelliferone and 1-naphthol glucuronides, while mrp3 exhibits stereoselective propranolol glucuronide transport. *lvfol Phann.* 2017; 14:3299-3311

56. Sun Y L, Hu S J, Wang L H, Hu Y, Zhou J Y. Effect of beta-blockers on cardiac function and calcium handling protein in postinfarction heart failure rats. *Chest.* 2005; 128:1812-1821

57. Mackiewicz U, Maczewski M, Konior A, Tellez J O, Nowis D, Dobrzynski H, Boyett M R, Lewartowski B. Sarcolemmal ca2+-atpase ability to transport ca2+ gradually diminishes after myocardial infarction in the rat. *Cardiovascular research.* 2009; 81:546-554

58. Lowes B D, Gilbert E M, Abraham W T, Minobe W A, Larrabee P, Ferguson D, Wolfel E E, Lindenfeld J, Tsvetkova T, Robertson A D, Quaife R A, Bristow M R. Myocardial gene expression in dilated cardiomyopathy treated with beta-blocking agents. *N Engl J Med.* 2002; 346: 1357-1365

The invention claimed is:

1. A method for treating heart failure, the method comprising:

(a) assessing a responsiveness to beta-blocker treatment for a subject diagnosed with heart failure, wherein assessing comprises:

(1) detecting in a biological sample from said subject the presence or absence of a plurality of alleles, the plurality of alleles being located at a plurality of independent loci, wherein the plurality of independent loci correspond to a plurality of single nucleotide polymorphisms (SNPs), wherein the plurality of SNPs comprises ref SNP ID nos. rs4331189, rs4075503, rs16870234, rs75087282, rs28548659, rs782760, rs367841, rs6013374, rs189508091, rs299453, rs299445, rs9737956, rs6773175, rs34912, rs2457492, rs2225686, rs299468, rs34221557, rs60529740, rs10810237, rs10756612, rs4808387, rs56098448, rs34335569, rs1399958, rs62521322, rs2666763, rs4681163, rs12988451, rs6828706, rs60971978, rs4527059, rs2527834, rs12528081, rs4413992, rs4514425, rs4934638, rs10416900, rs61797384, rs2171574, rs34854, rs60764725, rs10518335, and rs6577189, (2) calculating a polygenic response predictor (PRP) score for said subject in accordance with Formula (I)

$$\text{score} = \sum_{j=1}^{x} w_j * SNP_j \qquad \text{Formula (I)}$$

wherein the PRP score is calculated on the basis of a set of SNPs in the plurality of SNPs wherein the set of SNPs consists of ref SNP ID nos. rs4331189, rs4075503, rs16870234, rs75087282, rs28548659, rs782760, rs367841, rs6013374, rs189508091, rs299453, rs299445, rs9737956, rs6773175, rs34912, rs2457492, rs2225686, rs299468, rs34221557, rs60529740, rs10810237, rs10756612, rs4808387, rs56098448, rs34335569, rs1399958, rs62521322, rs2666763, rs4681163, rs12988451, rs6828706, rs60971978, rs4527059, rs2527834, rs12528081, rs4413992, rs4514425, rs4934638, rs10416900, rs61797384, rs2171574, rs34854, rs60764725, rs10518335, and rs6577189, and then, adding the products to provide a sum, the sum representing the PRP score, and (3) identifying the subject as being a responder to beta-blocker treatment when the PRP score is less than 68, when at least 41 SNPs of 44 SNPs are used in Formula (I), and (b) treating the subject identified as being the responder to beta-blocker treatment with a beta-blocker, wherein the heart failure treatment comprises administration of a therapeutically effective amount of said beta-blocker.

2. The method of claim 1, wherein the subject has been diagnosed with New York Heart Association Class I heart failure.

3. The method of claim 1, wherein the subject has been diagnosed with New York Heart Association Class II heart failure.

4. The method of claim 1, wherein detecting the presence or absence of the plurality of alleles is achieved by amplification of a nucleic acid from said sample.

5. The method of claim 4, wherein amplification comprises polymerase chain reaction (PCR).

6. The method of claim 5, wherein primers for amplification are located on a chip.

7. The method of claim 6, wherein said primers for amplification are specific for the plurality of alleles.

8. The method of claim 4, wherein the amplification comprises:

a) admixing an amplification primer or amplification primer pair with a nucleic acid isolated from the biological sample, wherein the primer or primer pair is complementary or partially complementary to a region proximal to or including the single nucleotide polymorphism, and is capable of initiating nucleic acid polymerization by a polymerase on the nucleic acid; and, b) extending the primer or primer pair in a DNA polymerization reaction comprising a polymerase and the nucleic acid to generate an amplicon.

9. The method of claim 8, wherein the amplicon is detected by a process that includes one or more of: hybridizing the amplicon to an array, digesting the amplicon with a restriction enzyme, or real-time PCR analysis.

10. The method of claim 4, wherein the amplification comprises performing PCR, reverse transcriptase PCR (RT-PCR), or a ligase chain reaction (LCR) using a nucleic acid isolated from the biological sample as a template in the PCR, RT-PCR, or LCR.

11. The method of claim 4, further comprising cleaving amplified nucleic acid.

12. The method of claim 4, wherein said sample is derived from saliva or blood.

13. The method according to claim 1, wherein detecting the presence or absence of the plurality of alleles is achieved by whole genome sequencing of a nucleic acid from said biological sample.

14. The method of claim 1, wherein the treatment comprises administration of a beta-blocker medicament that is selected from the group consisting of acebutolol, atenolol, betaxolol, bisoprolol fumarate, carteolol, carvedilol, esmolol, labetalol, metoprolol, nadolol, nebivolol, penbutolol, pindolol, propranolol, sotalol, timolol, and/or timolol ophthalmic solution.

15. The method of claim 1, further comprising the step of recording the results of said detecting on a computer readable medium.

16. The method of claim 15, wherein said results are communicated to the subject or to a physician of the subject.

17. The method of claim 15, wherein said results are recorded in the form of a report.

* * * * *